(12) United States Patent
Buschmann et al.

(10) Patent No.: US 8,921,388 B2
(45) Date of Patent: Dec. 30, 2014

(54) DIHYDROXYPYRIMIDINE CARBONIC ACID DERIVATIVES AND THEIR USE IN THE TREATMENT, AMELIORATION OR PREVENTION OF A VIRAL DISEASE

(71) Applicants: Savira Pharmaceuticals GMBH, Vienna (AT); F. Hoffmann-La Roche AG, Basel (CH); European Molecular Biology Laboratory, Heidelberg (DE)

(72) Inventors: Helmut Buschmann, Aachen (DE); Andrea Wolkerstorfer, Vienna (AT); Oliver Szolar, Vienna (AT); Norbert Handler, Vienna (AT); Stephen Cusack, Seyssinet (FR); Mark Smith, Jersey City, NJ (US); Sung-Sau So, Verona, NJ (US)

(73) Assignees: European Molecular Biology Laboratory, Heidelberg (DE); F. Hoffmann-La Roche AG, Basel (CH); Savira pharmaceuticals GmbH, Vienna (AT)

( * ) Notice: Subject to any disclaimer, the term of this patent is extended or adjusted under 35 U.S.C. 154(b) by 0 days.

(21) Appl. No.: 13/958,913

(22) Filed: Aug. 5, 2013

(65) Prior Publication Data

US 2014/0038990 A1 Feb. 6, 2014

Related U.S. Application Data

(60) Provisional application No. 61/679,968, filed on Aug. 6, 2012.

(51) Int. Cl.
| | |
|---|---|
| *A61P 35/00* | (2006.01) |
| *C07D 239/557* | (2006.01) |
| *A61K 31/513* | (2006.01) |
| *A61K 45/06* | (2006.01) |
| *C07D 403/06* | (2006.01) |
| *C07D 239/52* | (2006.01) |

(52) U.S. Cl.
CPC .......... *C07D 239/557* (2013.01); *A61K 31/513* (2013.01); *A61K 45/06* (2013.01); *C07D 403/06* (2013.01); *C07D 239/52* (2013.01)

USPC .......................................................... 514/294

(58) Field of Classification Search
None
See application file for complete search history.

(56) References Cited

U.S. PATENT DOCUMENTS

2014/0079666 A1* 3/2014 Webb et al. .................. 424/85.4

FOREIGN PATENT DOCUMENTS

| CN | 102 617 487 A | 8/2012 |
|---|---|---|
| CN | 102 911 124 A | 2/2013 |
| EP | 1 698 628 A1 | 9/2006 |
| WO | WO 03/035076 A1 | 5/2003 |
| WO | WO 03/035077 A1 | 5/2003 |
| WO | WO 03035076 A1 | 5/2003 |
| WO | WO 03035077 A1 | 5/2003 |
| WO | WO 2005/070901 A2 | 8/2005 |
| WO | WO 2005070901 A2 | 8/2005 |
| WO | WO 2011/046920 A1 | 4/2011 |
| WO | WO 2011046920 A1 | 4/2011 |
| WO | WO 2012/088283 A1 | 6/2012 |
| WO | WO 2012088283 A1 | 6/2012 |
| WO | WO 2012/151567 A1 | 11/2012 |
| WO | WO 2012151567 A1 | 11/2012 |

OTHER PUBLICATIONS

Edited by John M Coffin, Stephen H Hughes, and Harold E Varmus, Retroviruses, Cold Spring Harbor (NY): Cold Spring Harbor Laboratory Press; 1997. ISBN-10: 0-87969-571-4.*
Hisaki et al., "Synthesis and Anti-Influenza Virus Activity of Novel Pyrimidine Derivatives," *Antiviral Research*, vol. 42, No. 2, pp. 121-137 (1999).

* cited by examiner

*Primary Examiner* — San-Ming Hui
*Assistant Examiner* — Jeanmarie Calvillo
(74) *Attorney, Agent, or Firm* — Bryan Cave LLP

(57) ABSTRACT

The present invention relates to a compound having the general formula (Di), (Dii), or (Diii), optionally in the form of a pharmaceutically acceptable salt, solvate, polymorph, codrug, cocrystal, prodrug, tautomer, racemate, enantiomer, or diastereomer or mixture thereof,
which are useful in treating, ameliorating or preventing a viral disease. Furthermore, specific combination therapies are disclosed.

28 Claims, No Drawings

DIHYDROXYPYRIMIDINE CARBONIC ACID DERIVATIVES AND THEIR USE IN THE TREATMENT, AMELIORATION OR PREVENTION OF A VIRAL DISEASE

CROSS-REFERENCE TO RELATED APPLICATIONS

This application claims benefit to U.S. Provisional Application No. 61/679,968, filed Aug. 6, 2012. The contents of the above application are incorporated by reference as if recited in full herein.

FIELD OF THE INVENTION

The present invention relates to a compound having the general formula (Di), (Dii), or (Diii), optionally in the form of a pharmaceutically acceptable salt, solvate, polymorph, codrug, cocrystal, prodrug, tautomer, racemate, enantiomer, or diastereomer or mixture thereof, (Di)

$R^1—X^1$ ... (structure with $R^5$, $X^2$, $X^3$, $X^4—R^6$, N, N, L, $R^2$)

(Dii)

$R^1—X^1$ ... (structure with $R^5$, $X^2$, $X^3$, $X^5$, N, N, $R^3$, L, $R^2$)

(Diii)

$R^1—X^1$ ... (structure with $R^5$, $X^2$, $X^3$, $X^5$, $R^4$, N, N, L, $R^2$)

which is useful in treating, ameloriating or preventing a viral disease. Furthermore, specific combination therapies are disclosed.

BACKGROUND OF THE INVENTION

In recent years the serious threat posed by influenza virus to worldwide public health has been highlighted by, firstly, the ongoing low level transmission to humans of the highly pathogenic avian H5N1 strain (63% mortality in infected humans, http://www.who.int/csr/disease/avian_influenza/en/) and secondly, the unexpected emergence in 2009 of a novel pandemic strain A/H1N1 that has rapidly spread around the entire world (http://www.who.int/csr/disease/swineflu/en/). Whilst the new strain is highly contagious but currently only generally gives mild illness, the future evolution of this virus is unpredictable. In a much more serious, but highly plausible scenario, H5N1 could have been more easily transmissible between humans or the new A/H1N1 could have been more virulent and could have carried the single point mutation that confers Tamiflu resistance (Neumann et al., Nature, 2009 (18; 459(7249) 931-939)); as many seasonal H1N1 strains have recently done (Dharan et al., The Journal of the American Medical Association, 2009 Mar. 11; 301 (10), 1034-1041; Moscona et al., The New England Journal of Medicine, 2009 (Mar 5; 360(10) pp 953-956)). In this case, the delay in generating and deploying a vaccine (~6 months in the relatively favourable case of A/H1N1 and still not a solved problem for H5N1) could have been catastrophically costly in human lives and societal disruption.

It is widely acknowledged that to bridge the period before a new vaccine becomes available and to treat severe cases, as well as to counter the problem of viral resistance, a wider choice of anti-influenza drugs is required. Development of new anti-influenza drugs has therefore again become a high priority, having been largely abandoned by the major pharmaceutical companies once the anti-neuraminidase drugs became available.

An excellent starting point for the development of antiviral medication is structural data of essential viral proteins. Thus, the crystal structure determination of e.g. the influenza virus surface antigen neuraminidase (Von Itzstein, M. et al., (1993), Nature, 363, pp. 418-423) led directly to the development of neuraminidase inhibitors with anti-viral activity preventing the release of virus from the cells, however, not the virus production. These and their derivatives have subsequently developed into the anti-influenza drugs, zanamivir (Glaxo) and oseltamivir (Roche), which are currently being stockpiled by many countries as a first line of defence against an eventual pandemic. However, these medicaments provide only a reduction in the duration of the clinical disease. Alternatively, other anti-influenza compounds such as amantadine and rimantadine target an ion channel protein, i.e., the M2 protein, in the viral membrane interfering with the uncoating of the virus inside the cell. However, they have not been extensively used due to their side effects and the rapid development of resistant virus mutants (Magden, J. et al., (2005), Appl. Microbiol. Biotechnol., 66, pp. 612-621). In addition, more unspecific viral drugs, such as ribavirin, have been shown to work for treatment of influenza and other virus infections (Eriksson, B. et al., (1977), Antimicrob. Agents Chemother., 11, pp. 946-951). However, ribavirin is only approved in a few countries, probably due to severe side effects (Furuta et al., ANTIMICROBIAL AGENTS AND CHEMOTHERAPY, 2005, p. 981-986). Clearly, new antiviral compounds are needed, preferably directed against different targets.

Influenza virus as well as Thogotovirus belong to the family of Orthomyxoviridae which, as well as the family of the Bunyaviridae, including the Hantavirus, Nairovirus, Orthobunyavirus, and Phlebovirus, are negative stranded RNA viruses. Their genome is segmented and comes in ribonucleoprotein particles that include the RNA dependent RNA polymerase which carries out (i) the initial copying of the single-stranded virion RNA (vRNA) into viral mRNAs and (ii) the vRNA replication. This enzyme, a trimeric complex composed of subunits PA, PB1 and PB2, is central to the life cycle of the virus since it is responsible for the replication and transcription of viral RNA. In previous work the atomic structure of two key domains of the polymerase, the mRNA cap-binding domain in the PB2 subunit (Guilligay et al., Nature Structural & Molecular Biology 2008; May; 15(5): 500-506) and the endonuclease-active site in the PA subunit (Dias et al., Nature 2009, 458, 914-918) have been identified and determined. These two sites are critical for the unique cap-snatching mode of transcription that is used by influenza virus to generate viral mRNAs. For the generation of viral mRNA the polymerase makes use of the so called "cap-snatching" mechanism (Plotch, S. J. et al., (1981), Cell, 23, pp. 847-858; Kukkonen, S. K. et al (2005), Arch. Virol., 150, pp. 533-556; Leahy, M. B. et al, (2005), J. Virol., 71, pp. 8347-8351; Noah, D. L. et al., (2005), Adv. Virus Res., 65, pp. 121-145). A 5' cap (also termed an RNA cap, RNA 7-methylguanosine cap or an RNA m7G cap) is a modified guanine nucleotide that has been added to the 5' end of a messenger RNA. The 5' cap consists of a terminal 7-methylguanosine residue which is linked through a 5'-5'-triphosphate bond to the first transcribed nucleotide. The viral polymerase binds to the 5' RNA cap of cellular mRNA molecules and cleaves the RNA cap together with a stretch of 10 to 15 nucleotides. The capped RNA fragments then serve as primers for the synthesis of viral mRNA.

The polymerase complex seems to be an appropriate antiviral drug target since it is essential for synthesis of viral mRNA and viral replication and contains several functional active sites likely to be significantly different from those found in host cell proteins (Magden, J. et al., (2005), Appl. Microbiol. Biotechnol., 66, pp. 612-621). Thus, for example, there have been attempts to interfere with the assembly of polymerase subunits by a 25-amino-acid peptide resembling the PA-binding domain within PB1 (Ghanem, A. et al., (2007), J. Virol., 81, pp. 7801-7804). Furthermore, the endonuclease activity of the polymerase has been targeted and a series of 4-substituted 2,4-dioxobutanoic acid compounds has been identified as selective inhibitors of this activity in influenza viruses (Tomassini, J. et al., (1994), Antimicrob. Agents Chemother., 38, pp. 2827-2837). In addition, flutimide, a substituted 2,6-diketopiperazine, identified in extracts of *Delitschia confertaspora*, a fungal species, has been shown to inhibit the endonuclease of influenza virus (Tomassini, J. et al., (1996), Antimicrob. Agents Chemother., 40, pp. 1189-1193). Moreover, there have been attempts to interfere with viral transcription by nucleoside analogs, such as 2'-deoxy-2'-fluoroguanosine (Tisdale, M. et al., (1995), Antimicrob. Agents Chemother., 39, pp. 2454-2458).

Certain heterocyclic carboxamides which are stated to be useful in preventing or treating atherosclerosis or restenosis are disclosed in WO 2004/019933. The compounds are stated to be useful in these applications due to their activity against herpes viruses because atherosclerosis is related to a number of herpes virus infections.

WO 2011/046920 refers to DXR inhibitors which are stated to be suitable for antimicrobial therapy.

B. M. Baughman et al. identify influenza endonuclease inhibitors using a fluorescence polarization assay (*ACS Chem. Biol.* 2012, 7, 526-534).

It is an object of the present invention to identify further compounds which are effective against viral diseases and which have improved pharmacological properties.

SUMMARY OF THE INVENTION

Accordingly, in a first embodiment, the present invention provides a compound having the general formula (Di), (Dii), or (Diii).

It is understood that throughout the present specification the term "a compound having the general formula (Di), (Dii), or (Diii)" encompasses pharmaceutically acceptable salts, solvates, polymorphs, prodrugs, codrugs, cocrystals, tautomers, racemates, enantiomers, or diastereomers or mixtures thereof unless mentioned otherwise.

A further embodiment of the present invention relates to a pharmaceutical composition comprising a compound having the general formula (Di), (Dii), or (Diii) and optionally one or more pharmaceutically acceptable excipient(s) and/or carrier(s).

The compounds having the general formula (Di), (Dii), or (Diii) are useful for treating, ameliorating or preventing viral diseases.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Definitions

The term "alkyl" refers to a saturated straight or branched carbon chain.

The term "cycloalkyl" represents a cyclic version of "alkyl". The term "cycloalkyl" is also meant to include bicyclic, tricyclic and polycyclic versions thereof. Unless specified otherwise, the cycloalkyl group can have 3 to 12 carbon atoms.

The term "cyclic heteroalkyl" includes monocyclic, bicyclic, tricyclic and polycyclic heteroalkyl groups. Unless specified otherwise, the cyclic heteroalkyl group can have 3 to 12 atoms and can include one or more heteroatoms selected from N, O or S.

"Hal" or "halogen" represents F, Cl, Br and I.

The term "aryl" preferably refers to an aromatic monocyclic ring containing 6 carbon atoms, an aromatic bicyclic ring system containing 10 carbon atoms or an aromatic tricyclic ring system containing 14 carbon atoms. Examples are phenyl, naphthyl or anthracenyl, preferably phenyl.

The term "heteroaryl" preferably refers to a five- or six-membered aromatic ring wherein one or more of the carbon atoms in the ring have been replaced by 1, 2, 3, or 4 (for the five-membered ring) or 1, 2, 3, 4, or 5 (for the six-membered ring) of the same or different heteroatoms, whereby the heteroatoms are selected from O, N and S. Examples of the heteroaryl group include pyrrole, pyrrolidine, oxolane, furan, imidazolidine, imidazole, pyrazole, oxazolidine, oxazole, thiazole, piperidine, pyridine, morpholine, piperazine, and dioxolane.

The term "hydrocarbon group which contains from 5 to 20 carbon atoms and optionally 1 to 4 heteroatoms selected from O, N and S and which contains at least one ring" refers to any group having 5 to 20 carbon atoms and optionally 1 to 4 heteroatoms selected from O, N and 2 as long as the group contains at least one ring. The term is also meant to include bicyclic, tricyclic and polycyclic versions thereof. If more than one ring is present, they can be separate from each other or be annulated. The ring(s) can be either carbocyclic or heterocyclic and can be saturated, unsaturated or aromatic. The carbon atoms and heteroatoms can either all be present in the one or more rings or some of the carbon atoms and/or heteroatoms can be present outside of the ring, e.g., in a linker group (such as —(CH$_2$)$_p$— with p=1 to 6). Examples of these groups include -(optionally substituted C$_{3-7}$ cycloalkyl), -(optionally substituted aryl) wherein the aryl group can be, for example, phenyl, -(optionally substituted biphenyl), adamantyl, —(C$_{3-7}$ cycloalkyl)-aryl as well as the corresponding compounds with a linker. Further examples of these groups include -(optionally substituted 3 to 7 membered cyclic heteroalkyl) or -(optionally substituted heteroaryl) containing, for instance, 1 to 3 N atoms.

The term "(optionally substituted mono- or polycyclic group containing 3 to 20 carbon atoms and optionally 1 to 4 heteroatoms selected from O, N and S)" refers to any mono- or polycyclic group containing 3 to 20 carbon atoms and optionally 1 to 4 heteroatoms selected from O, N and S. This term includes monocyclic, bicyclic, tricyclic and polycyclic versions thereof. If more than one ring is present, they can be separate from each other or be annulated. The ring(s) can be either carbocyclic or heterocyclic and can be saturated, unsaturated or aromatic. The carbon atoms and heteroatoms can either all be present in the one or more rings or some of the carbon atoms and/or heteroatoms can be present outside of the ring, e.g., in a linker group (such as —(CH$_2$)$_p$— with p=1 to 6). Examples of these groups include -(optionally substituted C$_{3-7}$ cycloalkyl), and -(optionally substituted aryl) wherein the aryl group can be, for example, phenyl or anthracenyl as well as the corresponding compounds with a linker.

If a compound or moiety is referred to as being "optionally substituted", it can in each instance include 1 or more of the indicated substituents, whereby the substituents can be the same or different.

The term "pharmaceutically acceptable salt" refers to a salt of a compound of the present invention. Suitable pharmaceutically acceptable salts include acid addition salts which may, for example, be formed by mixing a solution of compounds of the present invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like (see, for example, S. M. Berge et al., "Pharmaceutical Salts", J. Pharm. Sci., 66, pp. 1-19 (1977)).

When the compounds of the present invention are provided in crystalline form, the structure can contain solvent molecules. The solvents are typically pharmaceutically acceptable solvents and include, among others, water (hydrates) or organic solvents. Examples of possible solvates include ethanolates and iso-propanolates.

The term "codrug" refers to two or more therapeutic compounds bonded via a covalent chemical bond. A detailed definition can be found, e.g., in N. Das et al., European Journal of Pharmaceutical Sciences, 41, 2010, 571-588.

The term "cocrystal" refers to a multiple component crystal in which all components are solid under ambient conditions when in their pure form. These components co-exist as a stoichiometric or non-stoichiometric ratio of a target molecule or ion (i.e., compound of the present invention) and one or more neutral molecular cocrystal formers. A detailed discussion can be found, for example, in Ning Shan et al., Drug Discovery Today, 13(9/10), 2008, 440-446 and in D. J. Good et al., Cryst. Growth Des., 9(5), 2009, 2252-2264.

The compounds of the present invention can also be provided in the form of a prodrug, namely a compound which is metabolized in vivo to the active metabolite. Suitable prodrugs are, for instance, esters. Specific examples of suitable groups are given, among others, in US 2007/0072831 in paragraphs [0082] to [0118] under the headings prodrugs and protecting groups. If X$^1$ is O or S, preferred examples of the prodrug include compounds in which R$^1$ is replaced by one of the following groups:

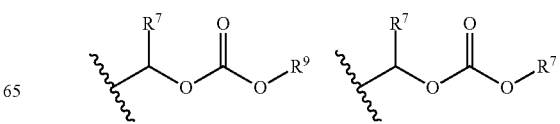

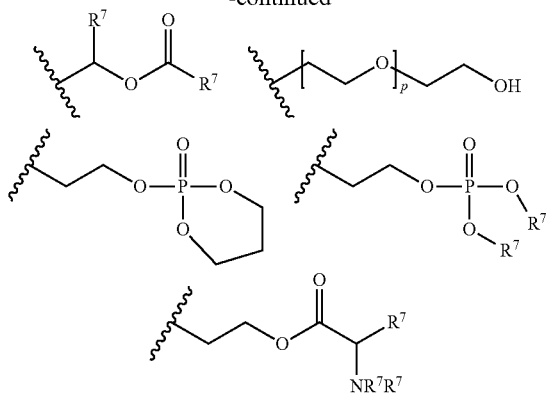

In these formulae, $R^7$ can be the same or different. $R^9$ is a cyclic group such as an aryl group or a $C_{3-7}$ cycloalkyl group. p is 2 to 8.

If $X^1$ is NR*, preferred examples of the prodrug include compounds in which $R^1$ and R* are not both H.

Compounds Having the General Formula (Di), (Dii), or (Diii)

The present invention provides a compound having the general formula (Di), (Dii), or (Diii).

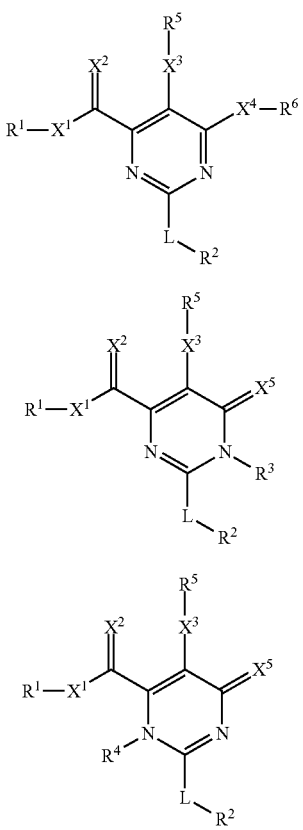

The present invention provides a compound having the general formula (Di), (Dii), or (Diii) in which the following definitions apply.

$X^1$ is O, S or NR*; preferably O, or NR*.
$X^2$ is O or S; preferably O.
$X^3$ is O or S; preferably O.
$X^4$ is O or S; preferably O.
$X^5$ is O or S; preferably O.
L is —$(CH_2)_m$—, —NR*—$SO_2$— or —$SO_2$—NR*—; preferably —$(CH_2)_m$— or —NR*—$SO_2$—.
m is 1 to 4; preferably m is 1 or 2; more preferably m is 1.
$R^1$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted aryl), —C(O)—O—R or —P(O)(OR)$_2$. If $X^1$ is NR* then $R^1$ and R* can optionally be bound together to form a 5- to 7-membered ring. Preferably $R^1$ is —H or -(optionally substituted $C_{1-6}$ alkyl).
$R^2$ is a hydrocarbon group which contains from 5 to 20 carbon atoms and optionally 1 to 4 heteroatoms selected from O, N and S and which contains at least one ring, wherein the hydrocarbon group can be optionally substituted. Preferably $R^2$ is an optionally substituted aryl, optionally substituted heteroaryl or optionally substituted $C_{5-7}$ cycloalkyl, more preferably $R^2$ is selected from

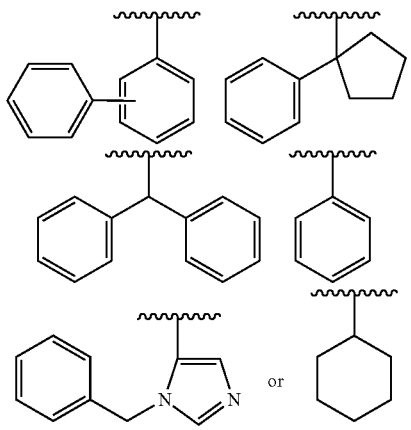

wherein the heterocyclic group, phenyl group, cyclohexyl group or cyclopentyl group can be optionally substituted in any available position by a substituent which is independently selected from —$C_{1-6}$ alkyl, halogen, —$CF_3$, —CN, —OH, and —O—$C_{1-6}$ alkyl.
$R^3$ is —H, -(optionally substituted $C_{1-6}$ alkyl), -(optionally substituted $C_{3-7}$ cycloalkyl), -(optionally substituted aryl), or —$C_{1-4}$ alkyl-(optionally substituted aryl).
$R^4$ is —H, -(optionally substituted $C_{1-6}$ alkyl), -(optionally substituted $C_{3-7}$ cycloalkyl), -(optionally substituted aryl), or —$C_{1-4}$ alkyl-(optionally substituted aryl).
$R^5$ is —H, —C(O)-(optionally substituted $C_{1-6}$ alkyl), or -(optionally substituted $C_{1-6}$ alkyl).
$R^6$ is —H, —C(O)-(optionally substituted $C_{1-6}$ alkyl), or -(optionally substituted $C_{1-6}$ alkyl).
R* is —H, or —($C_{1-6}$ alkyl); preferably —H.
R** is —H, —($C_{1-6}$ alkyl), —($C_{3-7}$ cycloalkyl), -(aryl), or —$C_{1-4}$ alkyl-(aryl); preferably —($C_{1-6}$ alkyl) or -(aryl).

The optional substituent of the alkyl group is selected from the group consisting of halogen, —CN, —NR*R*, —OH, and —O—$C_{1-6}$ alkyl:

The optional substituent of the cycloalkyl group, the aryl group or the hydrocarbon group is selected from the group consisting of —$C_{1-6}$ alkyl, -halogen, —$CF_3$, —CN, —$X^1$—R*, -aryl and —$C_{1-4}$ alkyl-aryl.

The present inventors have surprisingly found that the compounds of the present invention which have a bulky, hydrophobic group represented by -L-$R^2$ have improved pharmacological properties compared to corresponding compounds which have a less space demanding group in this position. Without wishing to be bound by theory, it is assumed that the viral polymerase protein has a pocket for binding and that this hydrophobic group of the compounds of the present invention has improved binding compared to other groups. This could not have been predicted or expected based on the art.

The compounds of the present invention can be administered to a patient in the form of a pharmaceutical composition which can optionally comprise one or more pharmaceutically acceptable excipient(s) and/or carrier(s).

The compounds of the present invention can be administered by various well known routes, including oral, rectal, intragastrical, intracranial and parenteral administration, e.g. intravenous, intramuscular, intranasal, intradermal, subcutaneous, and similar administration routes. Oral, intranasal and parenteral administration are particularly preferred. Depending on the route of administration different pharmaceutical formulations are required and some of those may require that protective coatings are applied to the drug formulation to prevent degradation of a compound of the invention in, for example, the digestive tract.

Thus, preferably, a compound of the invention is formulated as a syrup, an infusion or injection solution, a spray, a tablet, a capsule, a capslet, lozenge, a liposome, a suppository, a plaster, a band-aid, a retard capsule, a powder, or a slow release formulation. Preferably, the diluent is water, a buffer, a buffered salt solution or a salt solution and the carrier preferably is selected from the group consisting of cocoa butter and vitebesole.

Particular preferred pharmaceutical forms for the administration of a compound of the invention are forms suitable for injectionable use and include sterile aqueous solutions or dispersions and sterile powders for the extemporaneous preparation of sterile injectable solutions or dispersions. In all cases the final solution or dispersion form must be sterile and fluid. Typically, such a solution or dispersion will include a solvent or dispersion medium, containing, for example, water-buffered aqueous solutions, e.g. biocompatible buffers, ethanol, polyol, such as glycerol, propylene glycol, polyethylene glycol, suitable mixtures thereof, surfactants or vegetable oils. A compound of the invention can also be formulated into liposomes, in particular for parenteral administration. Liposomes provide the advantage of increased half-life in the circulation, if compared to the free drug and a prolonged more even release of the enclosed drug.

Sterilization of infusion or injection solutions can be accomplished by any number of art recognized techniques including but not limited to addition of preservatives like anti-bacterial or anti-fungal agents, e.g. parabene, chlorobutanol, phenol, sorbic acid or thimersal. Further, isotonic agents, such as sugars or salts, in particular sodium chloride, may be incorporated in infusion or injection solutions.

Production of sterile injectable solutions containing one or several of the compounds of the invention is accomplished by incorporating the respective compound in the required amount in the appropriate solvent with various ingredients enumerated above as required followed by sterilization. To obtain a sterile powder the above solutions are vacuum-dried or freeze-dried as necessary. Preferred diluents of the present invention are water, physiological acceptable buffers, physiological acceptable buffer salt solutions or salt solutions. Preferred carriers are cocoa butter and vitebesole. Excipients which can be used with the various pharmaceutical forms of a compound of the invention can be chosen from the following non-limiting list:

a) binders such as lactose, mannitol, crystalline sorbitol, dibasic phosphates, calcium phosphates, sugars, microcrystalline cellulose, carboxymethyl cellulose, hydroxyethyl cellulose, polyvinyl pyrrolidone and the like;
b) lubricants such as magnesium stearate, talc, calcium stearate, zinc stearate, stearic acid, hydrogenated vegetable oil, leucine, glycerids and sodium stearyl fumarates,
c) disintegrants such as starches, croscarmellose, sodium methyl cellulose, agar, bentonite, alginic acid, carboxymethyl cellulose, polyvinyl pyrrolidone and the like.

In one embodiment the formulation is for oral administration and the formulation comprises one or more or all of the following ingredients: pregelatinized starch, talc, povidone K 30, croscarmellose sodium, sodium stearyl fumarate, gelatin, titanium dioxide, sorbitol, monosodium citrate, xanthan gum, titanium dioxide, flavoring, sodium benzoate and saccharin sodium.

If a compound of the invention is administered intranasally in a preferred embodiment, it may be administered in the form of a dry powder inhaler or an aerosol spray from a pressurized container, pump, spray or nebulizer with the use of a suitable propellant, e.g., dichlorodifluoromethane, trichlorofluoromethane, dichlorotetrafluoroethane, a hydrofluoroalkane such as 1,1,1,2-tetrafluoroethane (HFA 134A™) or 1,1,1,2, 3,3,3-heptafluoropropane (HFA 227EA™), carbon dioxide, or another suitable gas. The pressurized container, pump, spray or nebulizer may contain a solution or suspension of the compound of the invention, e.g., using a mixture of ethanol and the propellant as the solvent, which may additionally contain a lubricant, e.g., sorbitan trioleate.

Other suitable excipients can be found in the Handbook of Pharmaceutical Excipients, published by the American Pharmaceutical Association, which is herein incorporated by reference.

It is to be understood that depending on the severity of the disorder and the particular type which is treatable with one of the compounds of the invention, as well as on the respective patient to be treated, e.g. the general health status of the patient, etc., different doses of the respective compound are required to elicit a therapeutic or prophylactic effect. The determination of the appropriate dose lies within the discretion of the attending physician. It is contemplated that the dosage of a compound of the invention in the therapeutic or prophylactic use of the invention should be in the range of about 0.1 mg to about 1 g of the active ingredient (i.e. compound of the invention) per kg body weight. However, in a preferred use of the present invention a compound of the invention is administered to a subject in need thereof in an amount ranging from 1.0 to 500 mg/kg body weight, preferably ranging from 1 to 200 mg/kg body weight. The duration of therapy with a compound of the invention will vary, depending on the severity of the disease being treated and the condition and idiosyncratic response of each individual patient. In one preferred embodiment of a prophylactic or therapeutic use, from 10 mg to 200 mg of the compound are orally administered to an adult per day, depending on the severity of the disease and/or the degree of exposure to disease carriers.

As is known in the art, the pharmaceutically effective amount of a given composition will also depend on the administration route. In general, the required amount will be higher if the administration is through the gastrointestinal tract, e.g., by suppository, rectal, or by an intragastric probe, and lower if the route of administration is parenteral, e.g., intravenous. Typically, a compound of the invention will be administered in ranges of 50 mg to 1 g/kg body weight, preferably 10 mg to 500 mg/kg body weight, if rectal or intragastric administration is used and in ranges of 1 to 100 mg/kg body weight if parenteral administration is used. For intranasal administration, 1 to 100 mg/kg body weight are envisaged.

If a person is known to be at risk of developing a disease treatable with a compound of the invention, prophylactic administration of the biologically active blood serum or the pharmaceutical composition according to the invention may be possible. In these cases the respective compound of the invention is preferably administered in above outlined preferred and particular preferred doses on a daily basis. Preferably, from 0.1 mg to 1 g/kg body weight once a day, preferably 10 to 200 mg/kg body weight. This administration can be continued until the risk of developing the respective viral disorder has lessened. In most instances, however, a compound of the invention will be administered once a disease/disorder has been diagnosed. In these cases it is preferred that a first dose of a compound of the invention is administered one, two, three or four times daily.

The compounds of the present invention are particularly useful for treating, ameliorating, or preventing viral diseases. The type of viral disease is not particularly limited. Examples of possible viral diseases include, but are not limited to, viral diseases which are caused by Poxyiridae, Herpesviridae, Adenoviridae, Papillomaviridae, Polyomaviridae, Parvoviridae, Hepadnaviridae, Retroviridae, Reoviridae, Filoviridae, Paramyxoviridae, Rhabdoviridae, Orthomyxoviridae, Bunyaviridae, Arenaviridae, Coronaviridae, Picornaviridae, Hepeviridae, Caliciviridae, Astroviridae, Togaviridae, Flaviviridae, Deltavirus, Bornaviridae, and prions. Preferably viral diseases which are caused by Herpesviridae, Retroviridae, Filoviridae, Paramyxoviridae, Rhabdoviridae, Orthomyxoviridae, Bunyaviridae, Arenaviridae, Coronaviridae, Picornaviridae, Togaviridae, Flaviviridae, more preferably viral diseases which are caused by orthomyxoviridae.

Examples of the various viruses are given in the following table.

| Family | Virus (preferred examples) |
| --- | --- |
| Poxviridae | Smallpox virus |
| | Molluscum contagiosum virus |
| Herpesviridae | Herpes simplex virus |
| | Varicella zoster virus |
| | Cytomegalovirus |
| | Epstein Barr virus |
| | Kaposi's sarcoma-associated herpesvirus |
| Adenoviridae | Human adenovirus A-F |
| Papillomaviridae | Papillomavirus |
| Polyomaviridae | BK-virus |
| | JC-Virsu |
| Parvoviridae | B19 virus |
| | Adeno associated virus 2/3/5 |
| Hepadnaviridae | Hepatitis B virus |
| Retroviridae | Human immunodeficiency virus types 1/2 |
| | Human T-cell leukemia virus |
| | Human foamy virus |
| Reoviridae | Reovirus 1/2/3 |
| | Rotavirus A/B/C |
| | Colorado tick fever virus |
| Filoviridae | Ebola virus |
| | Marburg virus |
| Paramyxoviridae | Parainfluenza virus 1-4 |
| | Mumps virus |
| | Measles virus |
| | Respiratory syncytial virus |
| | Hendravirus |
| Rhabdoviridae | Vesicular stomatitis virus |
| | Rabies virus |
| | Mokola virus |
| | European bat virus |
| | Duvenhage virus |
| Orthomyxoviridae | Influenza virus types A-C |
| Bunyaviridae | California encephalitis virus |
| | La Crosse virus |
| | Hantaan virus |
| | Puumala virus |
| | Sin Nombre virus |
| | Seoul virus |
| | Crimean-Congo hemorrhagic fever virus |
| | Sakhalin virus |
| | Rift valley virus |
| | Sandfly fever virus |
| | Uukuniemi virus |
| Arenaviridae | Lassa virus |
| | Lymphocytic choriomeningitis virus |
| | Guanarito virus |
| | Junin virus, |
| | Machupo virus |
| | Sabia virus |
| Coronaviridae | Human coronavirus |
| Picornaviridae | Human enterovirus types A-D (Poliovirus, Echovirus, Coxsackie virus A/B) |
| | Rhinovirus types A/B/C |
| | Hepatitis A virus |
| | Parechovirus |
| | Food and mouth disease virus |
| Hepeviridae | Hepatitis E virus |
| Caliciviridae | Norwalk virus |
| | Sapporo virus |
| Astroviridae | Human astrovirus 1 |
| Togaviridae | Ross River virus |
| | Chikungunya virus |
| | O'nyong-nyong virus |
| | Rubella virus |
| Flaviviridae | Tick-borne encephalitis virus |
| | Dengue virus |
| | Yellow Fever virus |
| | Japanese encephalitis virus |
| | Murray Valley virus |
| | St. Louis encephalitis virus |
| | West Nile virus |
| | Hepatitis C virus |
| | Hepatitis G virus |
| | Hepatitis GB virus |
| Deltavirus | Hepatitis deltavirus |
| Bornaviridae | Bornavirus |
| Prions | |

Preferably, the compounds of the present invention are employed to treat influenza. Within the present invention, the term "influenza" includes influenza A, B, C, isavirus and thogotovirus and also covers bird flu and swine flu. The subject to be treated is not particularly restricted and can be any vertebrate, such as birds and mammals (including humans).

Without wishing to be bound by theory it is assumed that the compounds of the present invention are capable of inhibiting endonuclease activity, particularly of the influenza virus. More specifically it is assumed that they directly interfere with the N-terminal part of the influenza PA protein, which harbours endonuclease activity. However, delivery of a compound into a cell may represent a problem depending on, e.g., the solubility of the compound or its capabilities to cross the cell membrane. The present invention not only shows that the claimed compounds have in vitro polymerase inhibitory activity but also in vivo antiviral activity.

A possible measure of the in vitro polymerase inhibitory activity of the compounds having the formula (Di), (Dii), (Diii), (A) and/or (C) is the FRET endonuclease activity assay disclosed herein. Preferably, the compounds exhibit a % reduction of at least about 50% at 25 µM in the FRET assay. In this context, the % reduction is the % reduction of the initial reaction velocity (v0) of substrate cleavage of compound-treated samples compared to untreated samples. Preferably, the compounds exhibit an $IC_{50}$ of at least about 40 μM, more preferably at least about 20 μM, in the FRET assay. The half maximal inhibitory concentration ($IC_{50}$) is a measure of the effectiveness of a compound in inhibiting biological or biochemical function and was calculated from the initial reaction velocities (v0) in a given concentration series ranging from maximum 100 μM to at least 2 nM.

A possible measure of the in vivo antiviral activity of the compounds having the formula (Di), (Dii), (Diii), (A) and/or (C) is the CPE assay disclosed herein. Preferably, the compounds exhibit a % reduction of at least about 30% at 50 μM. In this connection, the reduction in the virus-mediated cytopathic effect (CPE) upon treatment with the compounds was calculated as follows: The cell viability of infected-treated and uninfected-treated cells was determined using an ATP-based cell viability assay (Promega). The response in relative luminescent units (RLU) of infected-untreated samples was subtracted from the response (RLU) of the infected-treated samples and then normalized to the viability of the corresponding uninfected sample resulting in % CPE reduction. Preferably, the compounds exhibit an $IC_{50}$ of at least about 45 μM, more preferably at least about 10 μM, in the CPE assay. The half maximal inhibitory concentration ($IC_{50}$) is a measure of the effectiveness of a compound in inhibiting biological or biochemical function and was calculated from the RLU response in a given concentration series ranging from maximum 100 μM to at least 100 nM.

The compounds having the general formula (Di), (Dii), or (Diii) can be used in combination with one or more other medicaments. The type of the other medicaments is not particularly limited and will depend on the disorder to be treated. Preferably, the other medicament will be a further medicament which is useful in treating, ameliorating or preventing a viral disease, more preferably a further medicament which is useful in treating, ameliorating or preventing influenza.

The following combinations of medicaments are envisaged as being particularly suitable:

(i) The combination of endonuclease and cap-binding inhibitors (particularly targeting influenza). The endonuclease inhibitors are not particularly limited and can be any endonuclease inhibitor, particularly any viral endonuclease inhibitor. Preferred endonuclease inhibitors are those having the general formula (I) as defined in the U.S. application with the Ser. No. 61/550,045, filed on Oct. 21, 2011, the complete disclosure of which is incorporated by reference. In particular, all descriptions with respect to the general formula of the compounds according to U.S. 61/550, 045, the preferred embodiments of the various substituents as well as the medical utility and advantages of the compounds are incorporated herein by reference.

The compounds having the general formula (I) of this reference can optionally be in the form of a pharmaceutically acceptable salt, solvate, polymorph, codrug, cocrystal, prodrug, tautomer, racemate, enantiomer, or diastereomer or mixture thereof. They are defined as follows (wherein the definitions of the various moieties given in this earlier application apply):

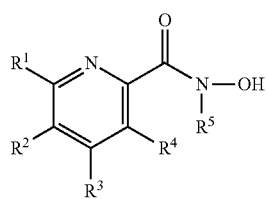

(I)

wherein
$R^1$ is selected from —H, —$C_{1-6}$ alkyl, —($C_{3-7}$ cycloalkyl) and —$CH_2$—($C_{3-7}$cycloalkyl);

$R^2$ is selected from —H,

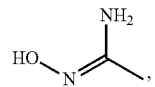

—$C_{1-6}$ alkyl, -Hal, —($C_{3-7}$ cycloalkyl), —$CH_2$—($C_{3-7}$ cycloalkyl), —$(CH_2)_m$-(optionally substituted aryl), -(optionally substituted 5- or 6-membered heterocyclic ring which contains at least one heteroatom selected from N, O and S, wherein the substituent is selected from —$C_{1-4}$ alkyl, -halogen, —CN, —$CHal_3$, -aryl, —$NR^6R^7$, and —$CONR^6R^7$;

$R^3$ is selected from —H, —$C_{1-6}$ alkyl,
—$(CH_2)_n$—$NR^6R^8$,
-(optionally substituted 5- or 6-membered carbo- or heterocyclic ring wherein the heterocyclic ring contains at least one heteroatom selected from N, O and S), wherein the substituent is selected from -Hal, —$C_{1-4}$ alkyl, —$NR^9R^{10}$, —$(CH_2)_n$—OH, —C(O)—$NR^9R^{10}$, —$SO_2$—$NR^9R^{10}$, —NH—C(O)—O—$R^{11}$, —C(O)—O—$R^{11}$, and a 5- or 6-membered heterocyclic ring which contains at least one heteroatom selected from N, O and S;

or wherein $R^1$ and $R^2$ together form a phenyl ring or wherein $R^2$ and $R^3$ together form a phenyl ring;

$R^4$ is —H;

$R^5$ is selected from the group consisting of —H or —$(CH_2)_n$-(optionally substituted aryl), wherein the substituent is selected from -Hal and —$C_{1-4}$ alkyl; or wherein $R^4$ and $R^5$ together form a methylene group —$CH_2$—, ethylene group —$CH_2CH_2$— or ethyne group —CHCH—, which can be optionally substituted by —$C_{1-4}$ alkyl, -halogen, —$CHal_3$, —$R^6R^7$, —$OR^6$, —$CONR^6R^7$, —$SO_2R^6R^7$, aryl or heteroaryl;

$R^6$ is selected from —H and —$C_{1-4}$ alkyl;
$R^7$ is selected from —H and —$C_{1-4}$ alkyl;
$R^8$ is selected from —H, —$C_{1-6}$ alkyl, —$(CH_2)_n$-(optionally substituted aryl), —$SO_2$—$(CH_2)_n$-(optionally substituted aryl), —$SO_2$—$(CH_2)_n$-(optionally substituted 5- to 10-membered mono- or bicyclic heteroring which contains at least one heteroatom selected from N, O and S), —$(CH_2)_n$-(optionally substituted 5- or 6-membered heterocyclic ring which contains at least one heteroatom selected from N, O and S), wherein the substituent is selected from -Hal, —$CF_3$, —$C_{1-4}$ alkyl, and —$(CH_2)_n$-aryl;

$R^9$ is selected from —H, —$C_{1-4}$ alkyl, and —$C_{1-4}$ alkylene-$NR^{11}R^{11}$;
$R^{10}$ is selected from —H, —$C_{1-4}$ alkyl, and —$C_{1-4}$ alkylene-$NR^{11}R^{11}$;
$R^{11}$ is selected from —H, —$CF_3$, and —$C_{1-4}$ alkyl;
each m is 0 or 1; and
each n is independently 0, 1, 2, or 3.

Further preferred endonuclease inhibitors are those having the general formula (A) as defined in the copending application with attorney's docket number T3448 US, the complete disclosure of which is incorporated by reference. In particular, all descriptions with respect to the general formula of the compounds having the general formula (A), the preferred embodiments of the various substituents as well as the medical utility and advantages of the compounds are incorporated herein by reference. The compounds having the general formula (A) can be optionally in the form of a pharmaceutically acceptable salt, solvate, polymorph, codrug, cocrystal, prodrug, tautomer, racemate, enantiomer, or diastereomer or mixture thereof. They are defined below.

Further preferred endonuclease inhibitors are those having the general formula (C) as defined in the copending application with attorney's docket number T3450 US, the complete disclosure of which is incorporated by reference. In particular, all descriptions with respect to the general formula of the compounds having the general formula (C), the preferred embodiments of the various substituents as well as the medical utility and advantages of the compounds are incorporated herein by reference. The compounds having the general formula (C) can be optionally in the form of a pharmaceutically acceptable salt, solvate, polymorph, codrug, cocrystal, prodrug, tautomer, racemate, enantiomer, or diastereomer or mixture thereof. They are defined below.

The cap-binding inhibitors are not particularly limited either and can be any cap-binding inhibitor, particularly any viral cap-binding inhibitor. Preferred cap-binding inhibitors are those having the general formula (II) as defined in U.S. application 61/550,057 and/or the compounds disclosed in WO2011/000566, the complete disclosure of which is incorporated by reference. In particular, all descriptions with respect to the general formula of the compounds according to U.S. 61/550,057 or WO2011/000566, the preferred embodiments of the various substituents as well as the medical utility and advantages of the compounds are incorporated herein by reference.

The compound having the general formula (II) can be optionally in the form of a pharmaceutically acceptable salt, solvate, polymorph, codrug, cocrystal, prodrug, tautomer, racemate, enantiomer, or diastereomer or mixture thereof. It is defined as follows:

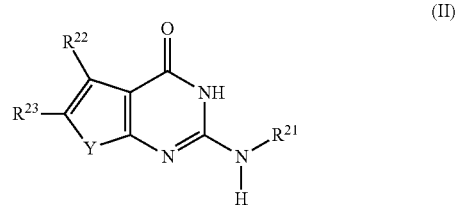

(II)

wherein
Y is S;
$R^{21}$ is selected from —H, —$C_{1-6}$alkyl, —$(CH_2)_q$-aryl, —$(CH_2)_q$-heterocyclyl, —$(CH_2)_q$-cycloalkyl, —$(CH_2)_p$—$OR^{25}$, and —$(CH_2)_p$—$NR^{25}R^{26}$;
$R^{22}$ is selected from —H, —$C_{1-6}$ alkyl, —$(CH_2)_q$-cycloalkyl, -Hal, —$CF_3$ and —CN;
$R^{23}$ is selected from -aryl, -heterocyclyl, -cycloalkyl, —C(—$R^{28}$)(—$R^{29}$)-aryl, —C(—$R^{28}$)(—$R^{29}$)-heterocyclyl, and —C(—$R^{28}$)(—$R^{29}$)-cycloalkyl;
$R^{25}$ is selected from —H, —$C_{1-6}$ alkyl, and —$(CH_2CH_2O)_rH$;
$R^{26}$ is selected from —H, and —$C_{1-6}$ alkyl;
$R^{27}$ is independently selected from —$C_{1-6}$ alkyl, —C(O)—$C_{1-6}$ alkyl, -Hal, —$CF_3$, —CN, —$COOR^{25}$, —$OR^{25}$, —$(CH_2)_q NR^{25}R^{26}$, —C(O)—$NR^{25}R^{26}$, and —$NR^{25}$—C(O)—$C_{1-6}$alkyl;
$R^{28}$ and $R^{29}$ are independently selected from —H, —$C_{1-6}$ alkyl, —$(CH_2)_q$-aryl, —$(CH_2)_q$-heterocyclyl, —$(CH_2)_q$-cycloalkyl, —OH, —O—$C_{1-6}$ alkyl, —O—$(CH_2)_q$-aryl, —O—$(CH_2)_q$-heterocyclyl, and —O—$(CH_2)_q$-cycloalkyl;

or $R^{28}$ and $R^{29}$ are together =O, —$CH_2CH_2$—, —$CH_2CH_2CH_2$—, or —$CH_2CH_2CH_2CH_2$—;
p is 1 to 4;
q is 0 to 4; and
r is 1 to 3;
wherein the aryl group, heterocyclyl group and/or cycloalkyl group can be optionally substituted with one or more substituents $R^{27}$.

The compounds of WO2011/000566 have the general formula (XXI):

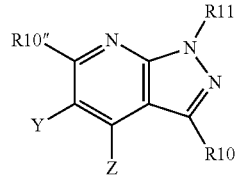

(XXI)

or a pharmaceutically effective salt, a solvate, a prodrug, a tautomer, a racemate, an enantiomer or a diastereomer thereof;
wherein
one of Y and Z is —$XR^{12}$ and the other is $R^{10'}$;
$R^{10}$, $R^{10'}$ and $R^{10''}$ are each individually selected from the group consisting of hydrogen, $C_1$-$C_6$-alkyl, $C_2$-$C_6$-alkenyl, $C_2$-$C_8$-alkynyl, —$(CH_2)_nC(O)OH$, —$(CH_2)_nC(O)OR^{16}$, —$(CH_2)_nOH$, —$(CH_2)_nOR^{16}$, —$CF_3$, —$(CH_2)_n$-cycloalkyl, —$(CH_2)_nC(O)NH_2$, —$(CH_2)_nC(O)NHR^{16}$, —$(CH_2)_nC(O)NR^{16}R^{17}$, —$(CH_2)_nS(O)_2NH_2$, —$(CH_2)_nS(O)_2NHR^{16}$, —$(CH_2)_nS(O)_2NR^{16}R^{17}$, —$(CH_2)_nS(O)_2R^{16}$, halogen, —CN, —$(CH_2)_n$-aryl, —$(CH_2)_n$-heteroaryl, —$(CH_2)_nNH_2$, —$(CH_2)_nNHR^{16}$, and —$(CH_2)_nNR^{16}R^{17}$; optionally substituted;
$R^{11}$ is selected from the group consisting of hydrogen, $C_1$-$C_6$-alkyl, —$CF_3$, $C_2$-$C_6$-alkenyl, $C_2$-$C_8$-alkynyl, —$(CH_2)_n$-cycloalkyl, —$(CH_2)_n$-aryl, —$(CH_2)_n$-heterocycloalkyl and —$(CH_2)_n$-heteroaryl; optionally substituted;
X is selected from the group consisting of $CH_2$, C(O), C(S), CH(OH), CH($OR^{16}$), $S(O)_2$, —$S(O)_2$—N(H)—, —$S(O)_2$—N($R^{16}$)—, —N(H)—$S(O)_2$—, —N($R^{16}$)—S(O)_2—, C(=NH), C(=N—$R^{16}$), CH($NH_2$), CH($NHR^{16}$), CH($NR^{16}R^{17}$), —C(O)—N(H)—, —C(O)—N($R^{16}$)—, —N(H)—C(O)—, —N($R^{16}$)—C(O)—, N(H), N(—$R^{16}$) and O;
$R^{12}$ is selected from the group consisting of $C_1$-$C_6$-alkyl, —$CF_3$, $C_2$-$C_6$-alkenyl, $C_2$-$C_8$-alkynyl, —$(CH_2)_n$-cycloalkyl, —$(CH_2)_n$-heterocycloalkyl, —$(CH_2)_n$-aryl, —$NR^{16}R^{17}$, and —$(CH_2)_n$-heteroaryl; optionally substituted;
$R^{16}$ and $R^{17}$ are independently selected from the group consisting of $C_1$-$C_6$-alkyl, $C_2$-$C_6$-alkenyl, $C_2$-$C_6$-alkynyl, —$(CH_2)_n$-cycloalkyl, —$(CH_2)_n$-aryl, —$CF_3$, —$C(O)R^{18}$ and —$S(O)_2R^{18}$; optionally substituted;
$R^{18}$ is independently selected from the group consisting of $C_1$-$C_6$-alkyl, $C_2$-$C_6$-alkenyl, $C_2$-$C_6$-alkynyl, —$(CH_2)_n$-cycloalkyl and —$CF_3$; optionally substituted; and
n is in each instance selected from 0, 1 and 2.

In the context of WO2011/000566 the term "optionally substituted" in each instance refers to between 1 and 10 substituents, e.g. 1, 2, 3, 4, 5, 6, 7, 8, 9, or 10 substituents which are in each instance preferably independently selected from the group consisting of halogen, in particular F, Cl, Br or I; —$NO_2$, —CN, —OR', —NR'R", —(CO)OR', —(CO)OR''', —(CO)NR'R'', —NR'COR'''', —NR'COR', —NR''CONR'R'', —NR''SO₂A, —COR'''; —SO₂NR'R'', —OOCR''', —CR''''OR''''OH, —R'''OH, =O, and -E;

R' and R'' are each independently selected from the group consisting of hydrogen, alkyl, alkenyl, alkynyl, —OE, cycloalkyl, heterocycloalkyl, aryl, heteroaryl, and aralkyl or together form a heteroaryl, or heterocycloalkyl; optionally substituted;

R''' and R'''' are each independently selected from the group consisting of alkyl, alkenyl, alkynyl, cycloalkyl, heterocycloalkyl, alkoxy, aryl, aralkyl, heteroaryl, and —NR'R''; and E is selected from the group consisting of alkyl, alkenyl, cycloalkyl, alkoxy, alkoxyalkyl, heterocycloalkyl, an alicyclic system, aryl and heteroaryl; optionally substituted.

Widespread resistance to both classes of licensed influenza antivirals (M2 ion channel inhibitors (adamantanes) and neuraminidase inhibitors (Oseltamivir)) occurs in both pandemic and seasonal viruses, rendering these drugs to be of marginal utility in the treatment modality. For M2 ion channel inhibitors, the frequency of viral resistance has been increasing since 2003 and for seasonal influenza A/H3N2, adamantanes are now regarded as ineffective. Virtually all 2009 H1N1 and seasonal H3N2 strains are resistant to the adamantanes (rimantadine and amantadine), and the majority of seasonal H1N1 strains are resistant to oseltamivir, the most widely prescribed neuraminidase inhibitor (NAI). For oseltamivir the WHO reported on significant emergence of influenza A/H1N1 resistance starting in the influenza season 2007/2008; and for the second and third quarters of 2008 in the southern hemisphere. Even more serious numbers were published for the fourth quarter of 2008 (northern hemisphere) where 95% of all tested isolates revealed no Oseltamivir-susceptibility. Considering the fact that now most national governments have been stockpiling Oseltamivir as part of their influenza pandemic preparedness plan, it is obvious that the demand for new, effective drugs is growing significantly. To address the need for more effective therapy, preliminary studies using double or even triple combinations of antiviral drugs with different mechanisms of action have been undertaken. Adamantanes and neuraminidase inhibitors in combination were analysed in vitro and in vivo and found to act highly synergistically. However, it is known that for both types of antivirals resistant viruses emerge rather rapidly and this issue is not tackled by combining these established antiviral drugs.

Influenza virus polymerase inhibitors are novel drugs targeting the transcription activity of the polymerase. Selective inhibitors against the cap-binding and endonuclease active sites of the viral polymerase severely attenuate virus infection by stopping the viral reproductive cycle. These two targets are located within distinct subunits of the polymerase complex and thus represent unique drug targets. Due to the fact that both functions are required for the so-called "cap-snatching" mechanism mandatory for viral transcription, concurrent inhibition of both functions is expected to act highly synergistically. This highly efficient drug combination would result in lower substance concentrations and hence improved dose-response-relationships and better side effect profiles.

Both of these active sites are composed of identical residues in all influenza A strains (e.g., avian and human) and hence this high degree of sequence conservation underpins the perception that these targets are not likely to trigger rapid resistant virus generation. Thus, endonuclease and cap-binding inhibitors individually and in combination are ideal drug candidates to combat both seasonal and pandemic influenza, irrespectively of the virus strain.

The combination of an endonuclease inhibitor and a cap-binding inhibitor or a dual specific polymerase inhibitor targeting both the endonuclease active site and the cap-binding domain would be effective against virus strains resistant against adamantanes and neuraminidase inhibitors and moreover combine the advantage of low susceptibility to resistance generation with activity against a broad range of virus strains.

(ii) The combination of inhibitors of different antiviral targets (particularly targeting influenza) focusing on the combination with (preferably influenza) polymerase inhibitors as dual or multiple combination therapy. Influenza virus polymerase inhibitors are novel drugs targeting the transcription activity of the polymerase. Selective inhibitors against the cap-binding and endonuclease active sites of the viral polymerase severely attenuate virus infection by stopping the viral reproductive cycle. The combination of a polymerase inhibitor specifically addressing a viral intracellular target with an inhibitor of a different antiviral target is expected to act highly synergistically. This is based on the fact that these different types of antiviral drugs exhibit completely different mechanisms of action and pharmacokinetics properties which act advantageously and synergistically on the antiviral efficacy of the combination.

This highly efficient drug combination would result in lower substance concentrations and hence improved dose-response-relationships and better side effect profiles. Moreover, advantages described under (i) for polymerase inhibitors would prevail for combinations of inhibitors of different antiviral targets with polymerase inhibitors.

Typically, at least one compound selected from the first group of polymerase inhibitors is combined with at least one compound selected from the second group of polymerase inhibitors.

The first group of polymerase inhibitors which can be used in this type of combination therapy includes, but is not limited to, the compounds having the formula (A) and/or (C).

The second group of polymerase inhibitors which can be used in this type of combination therapy includes, but is not limited to, the compounds having the general formula (I), the compounds having the general formula (II), the compounds disclosed in WO 2011/000566, WO 2010/110231, WO 2010/110409, WO 2006/030807 or U.S. Pat. No. 5,475,109 as well as flutimide and analogues, favipiravir and analogues, epigallocatechin gallate and analogues, as well as nucleoside analogs such as ribavirine.

(iii) The combination of polymerase inhibitors with neuramidase inhibitors

Influenza virus polymerase inhibitors are novel drugs targeting the transcription activity of the polymerase. Selective inhibitors against the cap-binding and endonuclease active sites of the viral polymerase severely attenuate virus infection by stopping the viral reproductive cycle. The combination of a polymerase inhibitor specifically addressing a viral intracellular target with an inhibitor of a different extracellular antiviral target, especially the (e.g., viral) neuraminidase is expected to act highly synergistically. This is based on the fact that these different types of antiviral drugs exhibit completely different mechanisms of action and pharmacokinetic properties which act advantageously and synergistically on the antiviral efficacy of the combination.

This highly efficient drug combination would result in lower substance concentrations and hence improved dose-response-relationships and better side effect profiles. Moreover, advantages described under (i) for polymerase inhibitors would prevail for combinations of inhibitors of different antiviral targets with polymerase inhibitors.

Typically, at least one compound selected from the above mentioned first group of polymerase inhibitors is combined with at least one neuramidase inhibitor.

The neuraminidase inhibitor (particularly influenza neuramidase inhibitor) is not specifically limited. Examples include zanamivir, oseltamivir, peramivir, KDN DANA, FANA, and cyclopentane derivatives.

(iv) The combination of polymerase inhibitors with M2 channel inhibitors

Influenza virus polymerase inhibitors are novel drugs targeting the transcription activity of the polymerase. Selective inhibitors against the cap-binding and endonuclease active sites of the viral polymerase severely attenuate virus infection by stopping the viral reproductive cycle. The combination of a polymerase inhibitor specifically addressing a viral intracellular target with an inhibitor of a different extracellular and cytoplasmic antiviral target, especially the viral M2 ion channel, is expected to act highly synergistically. This is based on the fact that these different types of antiviral drugs exhibit completely different mechanisms of action and pharmacokinetic properties which act advantageously and synergistically on the antiviral efficacy of the combination.

This highly efficient drug combination would result in lower substance concentrations and hence improved dose-response-relationships and better side effect profiles. Moreover, advantages described under (i) for polymerase inhibitors would prevail for combinations of inhibitors of different antiviral targets with polymerase inhibitors.

Typically, at least one compound selected from the above mentioned first group of polymerase inhibitors is combined with at least one M2 channel inhibitor.

The M2 channel inhibitor (particularly influenza M2 channel inhibitor) is not specifically limited. Examples include amantadine and rimantadine.

(v) The combination of polymerase inhibitors with alpha glucosidase inhibitors

Influenza virus polymerase inhibitors are novel drugs targeting the transcription activity of the polymerase. Selective inhibitors against the cap-binding and endonuclease active sites of the viral polymerase severely attenuate virus infection by stopping the viral reproductive cycle. The combination of a polymerase inhibitor specifically addressing a viral intracellular target, with an inhibitor of a different extracellular target, especially alpha glucosidase, is expected to act highly synergistically. This is based on the fact that these different types of antiviral drugs exhibit completely different mechanisms of action and pharmacokinetic properties which act advantageously and synergistically on the antiviral efficacy of the combination.

This highly efficient drug combination would result in lower substance concentrations and hence improved dose-response-relationships and better side effect profiles. Moreover, advantages described under (i) for polymerase inhibitors would prevail for combinations of inhibitors of different antiviral targets with polymerase inhibitors.

Typically, at least one compound selected from the above-mentioned first group of polymerase inhibitors is combined with at least one alpha glucosidase inhibitor.

The alpha glucosidase inhibitor (particularly influenza alpha glucosidase inhibitor) is not specifically limited. Examples include the compounds described in Chang et al., Antiviral Research 2011, 89, 26-34.

(vi) The combination of polymerase inhibitors with ligands of other influenza targets Influenza virus polymerase inhibitors are novel drugs targeting the transcription activity of the polymerase. Selective inhibitors against the cap-binding and endonuclease active sites of the viral polymerase severely attenuate virus infection by stopping the viral reproductive cycle. The combination of a polymerase inhibitor specifically addressing a viral intracellular target with an inhibitor of different extracellular, cytoplasmic or nucleic antiviral targets is expected to act highly synergistically. This is based on the fact that these different types of antiviral drugs exhibit completely different mechanisms of action and pharmacokinetic properties which act advantageously and synergistically on the antiviral efficacy of the combination.

This highly efficient drug combination would result in lower substance concentrations and hence improved dose-response-relationships and better side effect profiles. Moreover, advantages described under (i) for polymerase inhibitors would prevail for combinations of inhibitors of different antiviral targets with polymerase inhibitors.

Typically at least one compound selected from the above mentioned first group of polymerase inhibitors is combined with at least one ligand of another influenza target.

The ligand of another influenza target is not specifically limited. Examples include compounds acting on the sialidase fusion protein, e.g. Fludase (DAS181), siRNAs and phosphorothioate oligonucleotides, signal transduction inhibitors (ErbB tyrosine kinase, Abl kinase family, MAP kinases, PKCa-mediated activation of ERK signaling as well as interferon (inducers).

(vii) The combination of (preferably influenza) polymerase inhibitors with a compound used as an adjuvance to minimize the symptoms of the disease (antibiotics, anti-inflammatory agents like COX inhibitors (e.g., COX-1/COX-2 inhibitors, selective COX-2 inhibitors), lipoxygenase inhibitors, EP ligands (particularly EP4 ligands), bradykinin ligands, and/or cannabinoid ligands (e.g., CB2 agonists). Influenza virus polymerase inhibitors are novel drugs targeting the transcription activity of the polymerase. Selective inhibitors against the cap-binding and endonuclease active sites of the viral polymerase severely attenuate virus infection by stopping the viral reproductive cycle. The combination of a polymerase inhibitor specifically addressing a viral intracellular target with an compound used as an adjuvance to minimize the symptoms of the disease address the causative and symptomatic pathological consequences of viral infection. This combination is expected to act synergistically because these different types of drugs exhibit completely different mechanisms of action and pharmacokinetic properties which act advantageously and synergistically on the antiviral efficacy of the combination.

This highly efficient drug combination would result in lower substance concentrations and hence improved dose-response-relationships and better side effect profiles. Moreover, advantages described under (i) for polymerase inhibitors would prevail for combinations of inhibitors of different antiviral targets with polymerase inhibitors.

Compounds Having the General Formula (A)

The compounds having the general formula (A) are identified in the following.

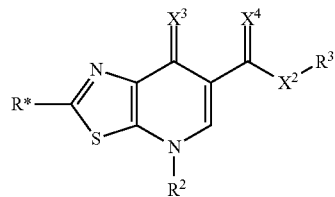

(A)

The present invention provides a compound having the general formula (A) in which the following definitions apply.
$R^*$ is —H, -Hal, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), —$C_{1-4}$ alkyl-(optionally substituted aryl) or —$X^1$—$R^1$. In a preferred embodiment, $R^*$ is -Hal, -(optionally substituted $C_{1-6}$ alkyl) (wherein the optional substituent of the alkyl group is preferably Hal, more preferably F); —$C_{1-4}$ alkyl-(optionally substituted aryl) (wherein the optional substituent of the aryl group is preferably halogen) or —$X^1$—$R^1$. In a more preferred embodiment $R^*$ is $X^1$—$R^1$.
$X^1$ is O, C(O), C(O)O, OC(O); S, SO, $SO_2$, $NR^4$, $N(R^5)C(O)$, $C(O)NR^5$, preferably $X^1$ is O, or $NR^4$, more preferably $X^1$ is $NR^4$. In one preferred embodiment, $X^1$ is $NR^4$ and $R^1$ and $R^4$ are joined together to form a 5- to 7-membered ring, which can optionally contain O, S or further N. In another preferred embodiment, $X^1$ is $NR^4$ and $R^1$ is —$SO_2$—$R^4$.
$X^2$ is O, S, $NR^4$, preferably $X^2$ is O.
$X^3$ is O or S, preferably $X^3$ is O.
$X^4$ is O or S, preferably $X^4$ is O.
$R^1$ is —H, -(optionally substituted $C_{1-6}$ alkyl), -(optionally substituted $C_{3-7}$ cycloalkyl), (optionally substituted aryl), —$C_{1-4}$ alkyl-(optionally substituted $C_{3-7}$ cycloalkyl), —$C_{1-4}$ alkyl-(optionally substituted aryl). Preferably $R^1$ is —H, -(optionally substituted $C_{1-6}$ alkyl), -(optionally substituted benzyl), more preferably $R^1$ is —H or -(optionally substituted benzyl). Throughout the present specification, it is understood that the definitions of the substituents of the aryl group apply analogously to the benzyl group.
$R^2$ is a hydrocarbon group which contains from 5 to 20 carbon atoms and optionally 1 to 4 heteroatoms selected from O, N and S and which contains at least one ring, wherein the hydrocarbon group can be optionally substituted. Preferably, the at least one ring is aromatic such as an aryl or heteroaryl ring. More preferably, $R^2$ is a hydrocarbon group which contains from 5 to 20 carbon atoms and optionally 1 to 4 heteroatoms and which contains at least two rings, wherein the hydrocarbon group can be optionally substituted. Even more preferably, at least one of the at least two rings is aromatic such as an aryl or heteroaryl ring. Preferred examples of $R^2$ can be selected from the group consisting of

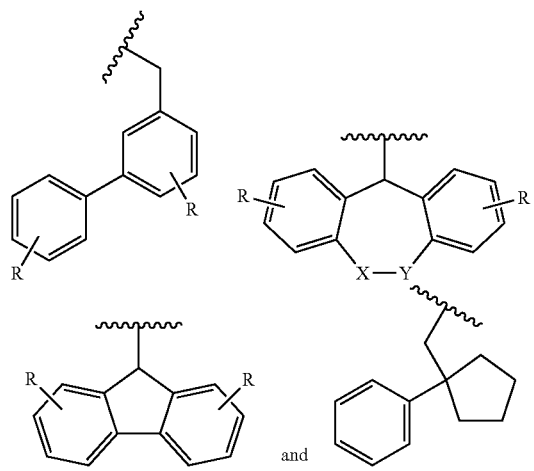

and wherein
X is absent, $CH_2$, NH, C(O)NH, S or O. Furthermore,
Y is $CH_2$.
In an alternative embodiment, X and Y can be joined together to form an annulated, carbo- or heterocylic 3- to 8-membered ring which can be saturated or unsaturated. Specific examples of X-Y include —$CH_2$—, —$CH_2$—$CH_2$—, —O—, and —NH—.
R is independently selected from H, —$C_{1-6}$ alkyl, halogen, —CN, —OH, and —O—$C_{1-6}$ alkyl.
$R^3$ is —H, -(optionally substituted $C_{1-6}$ alkyl), -(optionally substituted $C_{3-7}$ cycloalkyl), -(optionally substituted aryl), or —$C_{1-4}$ alkyl-(optionally substituted aryl) or if $X^2$ is $NR^4$, then $R^3$ can also be —OH, preferably $R^3$ is —H, —$C_{1-6}$ alkyl or Bz.
$R^4$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), or —$C_{1-4}$ alkyl-(optionally substituted aryl) or if $X^1$ is $NR^4$, then $R^4$ and $R^1$ can be joined together to form a 5- to 7-membered ring, which can optionally contain O, S or further N or if $X^2$ is $NR^4$, then $R^4$ and $R^3$ can be joined together to form a 5- to 7-membered ring, which can optionally contain O, S or further N. Preferably, $R^4$ is —H, -(optionally substituted aryl), or -(optionally substituted $C_{1-6}$ alkyl), more preferably, $R^4$ is —H or -(optionally substituted benzyl).
$R^5$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), or —$C_{1-4}$ alkyl-(optionally substituted aryl). Preferably, $R^5$ is —H.
$R^6$ is —H, or —$C_{1-6}$ alkyl.
The optional substituent of the alkyl group is selected from the group consisting of halogen, —CN, —$NR^6R^6$, —OH, and —O—$C_{1-6}$ alkyl. Preferably the substituent is -halogen, more preferably F.
The optional substituent of the cycloalkyl group, the aryl group or the hydrocarbon group is selected from the group consisting of —$C_{1-6}$ alkyl, halogen, —$CF_3$, —CN, —$X^1$—$R^5$ and —$C_{1-4}$ alkyl-aryl. Preferably, the substituent is -halogen (preferably F), —$OCH_3$ or —CN.

Compounds Having the General Formula (C)

The compounds having the general formula (C) are identified in the following.

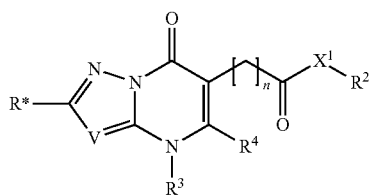

(C)

It is understood that throughout the present specification the term "a compound having the general formula (C)" encompasses pharmaceutically acceptable salts, solvates, polymorphs, prodrugs, tautomers, racemates, enantiomers, or diastereomers or mixtures thereof unless mentioned otherwise.

In the present invention the following definitions apply with respect to the compounds having the general formula (C).

V is N, or $CR^6$.

$X^1$ is O, S, or $NR^8$, preferably $X^1$ is O.

$X^2$ is $NR^5$, $N(R^5)C(O)$, $C(O)NR^5$, O, C(O), C(O)O, OC(O); S, SO, $SO_2$, $SO_2N(R^5)$ or $N(R^5)SO_2$. Preferably, $X^2$ is $NR^5$ or $N(R^5)SO_2$.

R* is —H, -Hal, -(optionally substituted $C_{1-6}$ alkyl), -(optionally substituted mono- or polycyclic group containing 3 to 20 carbon atoms and optionally 1 to 4 heteroatoms selected from O, N and S), —$C_{1-4}$ alkyl-(optionally substituted mono- or polycyclic group containing 3 to 20 carbon atoms and optionally 1 to 4 heteroatoms selected from O, N and S), or —$X^2$—$R^1$. Preferably R* is H, -(optionally substituted $C_{1-6}$ alkyl), -(optionally substituted $C_{3-7}$ cycloalkyl) or —$X^2$—$R^1$.

$R^1$ is —H, -(optionally substituted $C_{1-6}$ alkyl), -(optionally substituted mono- or polycyclic group containing 3 to 20 carbon atoms and optionally 1 to 4 heteroatoms selected from O, N and S), —$C_{1-4}$ alkyl-(optionally substituted mono- or polycyclic group containing 3 to 20 carbon atoms and optionally 1 to 4 heteroatoms selected from O, N and S). Preferably $R^1$ is —$C_{1-4}$ alkyl-(optionally substituted mono- or polycyclic group containing 3 to 20 carbon atoms and optionally 1 to 4 heteroatoms selected from O, N and S).

$R^2$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), or —$C_{1-4}$ alkyl-(optionally substituted aryl) or if $X^1$ is $NR^1$ then $R^2$ can also be —OH. Preferably, $R^2$ is —H or —$C_{1-6}$ alkyl.

$R^3$ is —H, —$R^7$, or —$X^2$—$R^7$. Preferably $R^3$ is —H, —$C_{1-4}$ alkyl-(optionally substituted aryl) or —$SO_2$—$R^5$. Preferably $R^3$ is —H.

$R^4$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), or —$C_{1-4}$ alkyl-(optionally substituted aryl). Preferably, $R^4$ is —H, or -(optionally substituted $C_{1-6}$ alkyl).

$R^5$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), or —$C_{1-4}$ alkyl-(optionally substituted aryl). Preferably $R^5$ is —$C_{1-4}$ alkyl-(optionally substituted aryl) or -(optionally substituted $C_{3-7}$ cycloalkyl).

$R^6$ H, —$C_{1-6}$ alkyl, -aryl, halogen or CN. Preferably, $R^6$ is H or -aryl.

$R^7$ is -(optionally substituted hydrocarbon group which contains from 5 to 20 carbon atoms and optionally 1 to 4 heteroatoms selected from O, N and S and which contains at least one ring). Preferably, $R^7$ is —$C_{1-4}$ alkyl-(optionally substituted aryl).

$R^8$ is —H, —$C_{1-6}$ alkyl or —$C_{1-4}$ alkyl-(optionally substituted aryl). Preferably, $R^8$ is —$C_{1-6}$ alkyl or —$C_{1-4}$ alkyl-(optionally substituted aryl).

n is 0 to 4, preferably 0 or 1.

The optional substituent of the alkyl group can be selected from the group consisting of halogen, —CN, —$NR^5R^5$, —OH, and —O—$C_{1-6}$ alkyl.

The optional substituent of the cycloalkyl group, the aryl group, the mono- or polycyclic group or the hydrocarbon group can be selected from the group consisting of —$C_{1-6}$ alkyl, halogen, —$CF_3$, —CN, —$X^2$—$C_{1-6}$ alkyl and —$C_{1-6}$ alkyl-aryl.

Various modifications and variations of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

The following examples are merely illustrative of the present invention and should not be construed to limit the scope of the invention as indicated by the appended claims in any way.

EXAMPLES

FRET Endonuclease Activity Assay

The influenza A virus (IAV) PA-Nter fragment (amino acids 1-209) harbouring the influenza endonuclease activity was generated and purified as described in Dias et al., Nature 2009; April 16; 458(7240), 914-918. The protein was dissolved in buffer containing 20 mM Tris pH 8.0, 100 mM NaCl and 10 mM β-mercaptoethanol and aliquots were stored at −20° C.

A 20 bases dual-labelled RNA oligo with 5'-FAM fluorophore and 3'-BHQ1 quencher was used as a substrate to be cleaved by the endonuclease activity of the PA-Nter. Cleavage of the RNA substrate frees the fluorophore from the quencher resulting in an increase of the fluorescent signal.

All assay components were diluted in assay buffer containing 20 mM Tris-HCl pH 8.0, 100 mM NaCl, 1 mM $MnCl_2$, 10 mM $MgCl_2$ and 10 mM β-mercaptoethanol. The final concentration of PA-Nter was 0.5 μM and 1.6 μM RNA substrate. The test compounds were dissolved in DMSO and generally tested at two concentrations or a concentration series resulting in a final plate well DMSO concentration of 0.5%. In those cases where the compounds were not soluble at that concentration, they were tested at the highest soluble concentration. SAV-6004 was used as a reference in the assay at a concentration of 0.1 μM.

5 μl of each compound dilution was provided in the wells of white 384-well microtiter plates (PerkinElmer) in eight replicates. After addition of PA-Nter dilution, the plates were sealed and incubated for 30 min at room temperature prior to the addition of 1.6 μM RNA substrate diluted in assay buffer. Subsequently, the increasing fluorescence signal of cleaved RNA was measured in a microplate reader (Synergy HT, Biotek) at 485 nm excitation and 535 nm emission wavelength. The kinetic read interval was 35 sec at a sensitivity of 35. Fluorescence signal data over a period of 20 min were used to calculate the initial velocity (v0) of substrate cleavage. Final readout was the % reduction of v0 of compound-treated samples compared to untreated. The half maximal inhibitory concentration ($IC_{50}$) is a measure of the effectiveness of a compound in inhibiting biological or biochemical function and was calculated from the initial reaction velocities (v0) in a given concentration series ranging from maximum 100 µM to at least 2 nM.

Cytopathic Effect (CPE) Assay

The influenza A virus (IAV) was obtained from American Tissue Culture Collection (A/Aichi/2/68 (H3N2); VR-547). Virus stocks were prepared by propagation of virus on Mardin-Darby canine kidney (MDCK; ATCC CCL-34) cells and infectious titres of virus stocks were determined by the 50% tissue culture infective dose ($TCID_{50}$) analysis as described in Reed, L. J., and H. Muench. 1938, Am. J. Hyg. 27:493-497.

MDCK cells were seeded in 96-well plates at $2 \times 10^4$ cells/well using DMEM/Ham's F-12 (1:1) medium containing 10% foetal bovine serum (FBS), 2 mM L-glutamine and 1% antibiotics (all from PAA). Until infection the cells were incubated for 5 hrs at 37° C., 5.0% $CO_2$ to form a ~80% confluent monolayer on the bottom of the well. Each test compound was dissolved in DMSO and generally tested at 25 µM and 250 µM. In those cases where the compounds were not soluble at that concentration they were tested at the highest soluble concentration. The compounds were diluted in infection medium (DMEM/Ham's F-12 (1:1) containing 5 µg/ml trypsin, and 1% antibiotics) for a final plate well DMSO concentration of 1%. The virus stock was diluted in infection medium (DMEM/Ham's F-12 (1:1) containing 5 µg/ml Trypsin, 1% DMSO, and 1% antibiotics) to a theoretical multiplicity of infection (MOI) of 0.05.

After removal of the culture medium and one washing step with PBS, virus and compound were added together to the cells. In the wells used for cytotoxicity determination (i.e. in the absence of viral infection), no virus suspension was added. Instead, infection medium was added. Each treatment was conducted in two replicates. After incubation at 37° C., 5% $CO_2$ for 48 hrs, each well was observed microscopically for apparent cytotoxicity, precipitate formation, or other notable abnormalities. Then, cell viability was determined using CellTiter-Glo luminescent cell viability assay (Promega). The supernatant was removed carefully and 65 µl of the reconstituted reagent were added to each well and incubated with gentle shaking for 15 min at room temperature. Then, 60 µl of the solution was transferred to an opaque plate and luminescence (RLU) was measured using Synergy HT plate reader (Biotek).

Relative cell viability values of uninfected-treated versus uninfected-untreated cells were used to evaluate cytotoxicity of the compounds. Substances with a relative viability below 80% at the tested concentration were regarded as cytotoxic and retested at lower concentrations.

Reduction in the virus-mediated cytopathic effect (CPE) upon treatment with the compounds was calculated as follows: The response (RLU) of infected-untreated samples was subtracted from the response (RLU) of the infected-treated samples and then normalized to the viability of the corresponding uninfected sample resulting in % CPE reduction. The half maximal inhibitory concentration ($IC_{50}$) is a measure of the effectiveness of a compound in inhibiting biological or biochemical function and was calculated from the RLU response in a given concentration series ranging from maximum 100 µM to at least 100 nM.

Example 1

Preparation of 1-phenyl-cyclopentanecarbonitrile

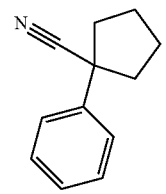 [SMILES: N#CC1(c2ccccc2)CCCC1]

To a suspension of NaH (11.3 g, 281.7 mmol, 60%) in DMSO (75 ml) were added dropwise a mixture of phenyl-acetonitrile (15 g, 128.0 mmol) and 1,4-dibromo-butane (18 ml, 128.0 mmol) dissolved in DMSO:Ether (150 ml, 1:1) at 0° C. and the reaction mixture was stirred at room temperature (RT) for 2 to 3 h. After completion of the reaction, water and 10% HCl solution were added to the crude mass. It was extracted with EtOAc. The organic layer was dried over $Na_2SO_4$, concentrated and purified by column chromatography (10% EtOAc-hexane) to get 1-phenyl-cyclopentanecarbonitrile (2) (19 g, 86.64%) as a yellow solid. MS: m/z=171 (MH+).

Example 2

Preparation of 1-phenyl-cyclopentanecarbaldehyde

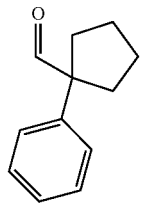 [SMILES: O=CC1(c2ccccc2)CCCC1]

To a solution of 1-phenyl-cyclopentanecarbonitrile (17 g, 99.4 mmol) in DCM (200 ml) was added diisobutylaluminium hydride (DIBAL) (140 ml, 25% in toluene, 248.5 mmol) very slowly. The mixture was stirred at −70° C. for 2 h. After completion of the reaction, it was slowly quenched by the addition of aqueous potassium sodium tartrate solution and then the mixture was stirred at RT for 16 h. It was then extracted with dichloromethane (DCM), washed with water, brine and dried with $Na_2SO_4$. The organic phase was concentrated to provide 1-phenyl-cyclopentanecarbaldehyde as a colorless liquid (15.5 g, crude).

Example 3

Preparation of (1-phenyl-cyclopentyl)-methanol

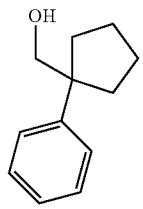 [SMILES: OCC1(c2ccccc2)CCCC1]

$NaBH_4$ (3.2 g, 86.2 mmol) was added portion wise to a cooled (ice bath) solution of 1-phenyl-cyclopentanecarbaldehyde (7.5 g, 43.1 mmol) in methanol (100 ml) and then stirred for 16 h at RT. After completion of the reaction, it was quenched with saturated ammonium chloride solution and the methanol under reduced pressure. The mixture was diluted with water, extracted with EtOAc, washed with water, brine, dried (Na$_2$SO$_4$) and evaporated to dryness under reduced pressure. Chromatography (15% EtOAc in hexanes) provided (1-phenyl-cyclopentyl)-methanol as a white solid (6 g, 79.8%).

Example 4

Preparation of methanesulfonic acid 1-phenyl-cyclopentylmethyl ester

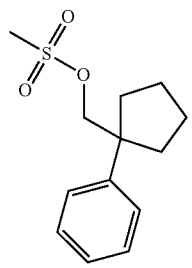 [SMILES: CS(=O)(=O)OCC1(c2ccccc2)CCCC1]

To a solution of (1-phenyl-cyclopentyl)-methanol (11.5 g, 64.34 mmol) in DCM (100 ml) was added TEA (17.5 ml, 130.68 mmol) and followed by methanesulfonyl chloride (MsCl) (8.9 g, 78.4 mmol) was added drop wise at 0° C. and the reaction mixture was stirred at RT for 16 h. After completion of the reaction, it was quenched with water and concentrated. Then the crude product was dissolved in DCM, extracted with DCM and the organic layer was washed with water, and brine and then dried over Na$_2$SO$_4$. The combined organic layer was concentrated to get crude methanesulfonic acid 1-phenyl-cyclopentylmethyl ester (10 g, crude) as a white solid.

Example 5

Preparation of (1-phenyl-cyclopentyl)-acetonitrile

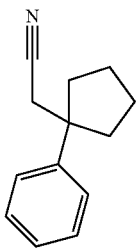 [SMILES: N#CCC1(c2ccccc2)CCCC1]

To a stirred solution of methanesulfonic acid 1-phenyl-cyclopentylmethyl ester (10 g, 39.37 mmol) in DMSO (30 ml) were added KI (0.6 g, 3.9 mmol) and NaCN (2.89 g, 59.05 mmol). It was then stirred at 140° C. for 16 h. After completion of the reaction, it was diluted with water, extracted with EtOAc and the organic layer was washed with water and brine. It was then dried over Na$_2$SO$_4$, concentrated and purified by normal column chromatography (15% EtOAc in hexanes) to afford the title compound as a colorless liquid (2.5 g, 34%).

Example 6

Preparation of 5-hydroxy-6-oxo-2-(1-phenyl-cyclopentylmethyl)-1,6-dihydro-pyrimidine-4-carboxylic acid methyl ester

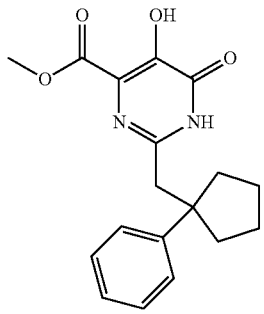 [SMILES: COC(=O)c1nc(CC2(c3ccccc3)CCCC2)[nH]c(=O)c1O]

A solution of potassium hydroxide (10.8 ml, 10.8 mmol) in methanol and hydroxylamine hydrochloride (10.8 ml, 10.8 mmol) in methanol were mixed, filtered and added to 2-(1-phenylcyclopentyl)acetonitrile (1 g, 5.4 mmol) in methanol (MeOH) and stirred at 60° C. for 24 h. It was then evaporated to dryness. The residue was dissolved in chloroform (30 ml) and to this was added dimethyl but-2-ynedioate (844 mg, 5.94 mmol). The reaction mixture was The mixture was stirred at 60° C. for 24 h, cooled and evaporated to dryness. The residue was dissolved in xylene (10 ml) and heated at 140° C. in a microwave oven for 1 h. The cooled residue was evaporated to dryness. Chromatography was conducted (40 g SiO$_2$; 10 to 70% EtOAc in hexanes). The residue was triturated with EtOAc, filtered and washed with Et$_2$O and dried under vacuum to give the title product as an off-white solid (0.110 g; 6%). LCMS: m/z=329 (MH+).

Example 7

Preparation of 5-hydroxy-6-oxo-2-(1-phenyl-cyclopentylmethyl)-1,6-dihydro-pyrimidine-4-carboxylic acid

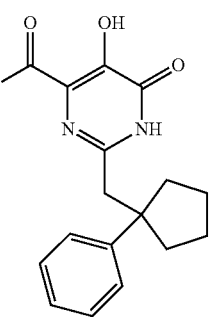

A solution of lithium hydroxide (7.66 mg, 320 μmol) in water (1.00 ml) was added to a stirred mixture of methyl 5,6-dihydroxy-2-((1-phenylcyclopentyl)methyl)pyrimidine-4-carboxylate (0.035 g, 107 μmol) in tetrahydrofuran (THF)

(4 ml). The mixture was stirred at RT for 72 h and then quenched with amberlyst (H+) IE resin, filtered and evaporated to dryness. The residue was triturated with EtOAc and dried under vacuum to give the title product as a white solid (0.012 g; 32%). LCMS: m/z=315 (MH+).

Example 8

Preparation of 5-hydroxy-6-oxo-2-(1-phenyl-cyclopentylmethyl)-1,6-dihydro-pyrimidine-4-carboxylic acid amide

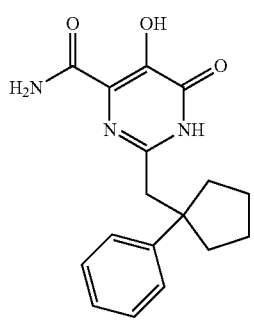

A solution of methyl 5,6-dihydroxy-2-((1-phenylcyclopentyl)methyl)pyrimidine-4-carboxylate (0.020 g, 60.9 µmol) in ammonia in MeOH (435 µl, 3.05 mmol) was heated at 100° C. for 20 min. The cooled solution was evaporated to dryness. The residue was diluted with MeOH and heated in the presence of Amberlyst resin (H+) until in solution. The material was filtered to remove the resin and evaporated to dryness. Trituration with MeOH followed by washing with Et₂O provided the desired product as a white solid (0.011 g; 49%). LCMS: m/z=314 (MH+).

Example 9

Preparation of 5-hydroxy-6-oxo-2-(1-phenyl-cyclopentylmethyl)-1,6-dihydro-pyrimidine-4-carboxylic acid methylamide

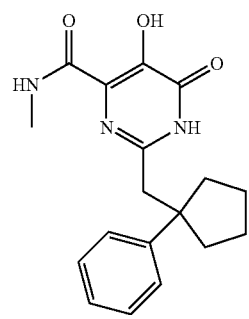 [SMILES: O=C(O)c1nc(CC2(c3ccccc3)CCCC2)[nH]c(=O)c1O]

To a solution of 5,6-dihydroxy-2-(1-phenyl-cyclopentylmethyl)-pyrimidine-4-carboxylic acid methyl ester (55 mg, 0.167 mmol) in THF (2 ml) was added 2M solution of methyl amine in THF (0.419 mL, 0.838 mmol) under nitrogen atmosphere in a microwave vessel. The reaction mixture was heated in a microwave oven at 110° C. for 10 min, then cooled and evaporated to dryness. The residue was washed with water and 30% ethyl acetate in hexane to get the title compound as an off-white solid (0.020 g, 36%). LCMS: m/z=327.8 (MH+).

Example 10

Preparation of 5-hydroxy-6-oxo-2-(1-phenyl-cyclopentylmethyl)-1,6-dihydro-pyrimidine-4-carboxylic acid benzylamide

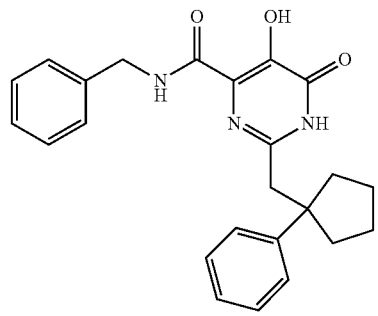 [SMILES: O=C(NCc1ccccc1)c1nc(CC2(c3ccccc3)CCCC2)[nH]c(=O)c1O]

5,6-Dihydroxy-2-(1-phenyl-cyclopentylmethyl)-pyrimidine-4-carboxylic acid benzylamide was synthesized as an off-white solid (20 mg, 30%) from 55 mg of 5,6-dihydroxy-2-(1-phenyl-cyclopentylmethyl)-pyrimidine-4-carboxylic acid methyl ester following the procedure described for 5-hydroxy-6-oxo-2-(1-phenyl-cyclopentylmethyl)-1,6-dihydro-pyrimidine-4-carboxylic acid methylamide (Example 9). LCMS: m/z=403.8 (MH+).

Example 11

Preparation of 5-hydroxy-1-methyl-6-oxo-2-(1-phenyl-cyclopentylmethyl)-1,6-dihydro-pyrimidine-4-carboxylic acid ethyl ester

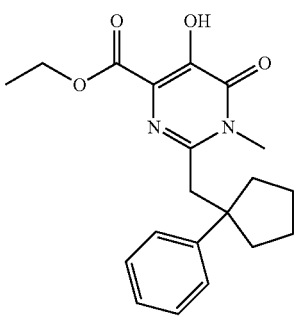 [SMILES: CCOC(=O)c1nc(CC2(c3ccccc3)CCCC2)n(C)c(=O)c1O]

5-Hydroxy-1-methyl-6-oxo-2-(1-phenyl-cyclopentylmethyl)-1,6-dihydro-pyrimidine-4-carboxylic acid ethyl ester was synthesized as a brown solid (35 mg, 20%) from 200 mg of 5-ethoxycarbonylmethyl-2-methyl-3-(1-phenyl-cyclopentylmethyl)-2,5-dihydro-[1,2,4]oxadiazole-5-carboxylic acid ethyl ester following the procedure described for 5-hydroxy-6-oxo-2-(1-phenyl-cyclopentylmethyl)-1,6-dihydro-pyrimidine-4-carboxylic acid methyl ester (Example 6). LCMS: m/z=357.0 (MH+).

Example 12

Preparation of 5-hydroxy-1-methyl-6-oxo-2-(1-phenyl-cyclopentylmethyl)-1,6-dihydro-pyrimidine-4-carboxylic acid

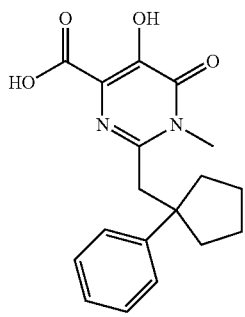 [SMILES: Cn1c(CC2(c3ccccc3)CCCC2)nc(C(=O)O)c(O)c1=O]

5-Hydroxy-1-methyl-6-oxo-2-(1-phenyl-cyclopentylmethyl)-1,6-dihydro-pyrimidine-4-carboxylic acid ethyl acid was synthesized as a white solid (30 mg, 23.2%) from 140 mg of 5-hydroxy-1-methyl-6-oxo-2-(1-phenyl-cyclopentylmethyl)-1,6-dihydro-pyrimidine-4-carboxylic acid ethyl ester following the procedure described for 5-hydroxy-6-oxo-2-(1-phenyl-cyclopentylmethyl)-1,6-dihydro-pyrimidine-4-carboxylic acid (Example 7). LCMS: m/z 327.0 (M-H).

Example 13

Preparation of 5-hydroxy-1-methyl-6-oxo-2-(1-phenyl-cyclopentylmethyl)-1,6-dihydro-pyrimidine-4-carboxylic acid methylamide

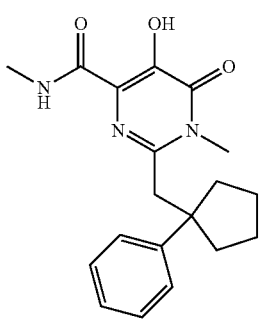 [SMILES: CNC(=O)c1nc(CC2(c3ccccc3)CCCC2)n(C)c(=O)c1O]

To a mixture of 5-hydroxy-1-methyl-6-oxo-2-(1-phenyl-cyclopentylmethyl)-1,6-dihydro-pyrimidine-4-carboxylic acid ethyl ester (175 mg, 0.491 mmol) and methyl amine (0.98 ml, 1.96 mmol, 2M in THF) was added a catalytic amount of Me$_3$Al under argon atmosphere in a sealed tube and it was heated at 60° C. for 16 h. After completion of the reaction, it was quenched with ice slowly and then extracted with EtOAc. The combined organic layer was then washed with water and brine. It was then dried over Na$_2$SO$_4$ and concentrated under vacuum. Purification by preparative HPLC provided the title compound as an off-white solid (40 mg, 24%). LCMS: m/z=342.0 (MH+).

Example 14

Preparation of 2-biphenyl-2-ylmethyl-5-hydroxy-1-methyl-6-oxo-1,6-dihydro-pyrimidine-4-carboxylic acid methyl ester

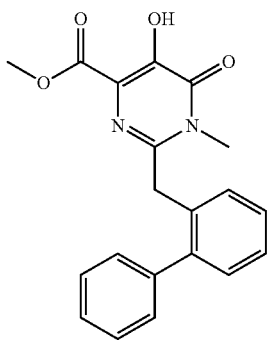 [SMILES: COC(=O)c1nc(Cc2ccccc2-c2ccccc2)n(C)c(=O)c1O]

A mixture containing 2-(biphenyl-2-yl)acetonitrile (2 g, 10.3 mmol), sodium carbonate (329 mg, 3.1 mmol) and N-methylhydroxylamine hydrochloride (432 mg, 5.17 mmol) in ethanol (5 ml) and water (5 ml) was heated at 80° C. for 2 h, cooled and treated with dimethyl but-2-ynedioate (809 mg, 5.69 mmol). The mixture was stirred at room temperature for 5 h and then diluted with EtOAc, washed with water and brine, dried (MgSO$_4$) and evaporated to dryness. Chromatography (40 g SiO$_2$, 10 to 60% EtOAc in hexanes) provided the 1,2,4-oxadiazoline intermediate as an orange oil. The oil was diluted in xylene (5.00 ml) and heated at 130° C. in a microwave oven for 3.5 h. The cooled mixture was diluted with EtOAc, washed with brine, dried (MgSO$_4$) and evaporated to dryness. Chromatography (24 g SiO$_2$; 20 to 60% EtOAc in hexanes) gave the title compound as a light brown foam (0.43 g; 81%). LCMS: m/z=351 (MH+).

Example 15

Preparation of 2-biphenyl-2-ylmethyl-5-hydroxy-1-methyl-6-oxo-1,6-dihydro-pyrimidine-4-carboxylic acid

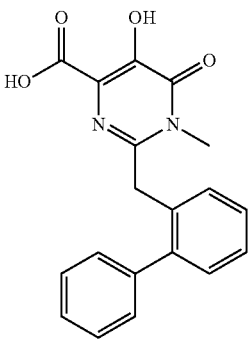 [SMILES: Cn1c(Cc2ccccc2-c2ccccc2)nc(C(=O)O)c(O)c1=O]

A solution of lithium hydroxide (8.2 mg, 342 µmol) in water was added to a stirred solution of methyl 2-(biphenyl-2-ylmethyl)-5-hydroxy-1-methyl-6-oxo-1,6-dihydropyrimidine-4-carboxylate (0.1 g, 285 µmol) in THF. After 24 h, the reaction was quenched by addition of 1M HCl, extracted into EtOAc, washed with brine, dried (MgSO$_4$) and evaporated.

Purification by preparative HPLC gave the desired product as a white solid (0.010 g; 10%). LCMS: m/z=337 (MH+).

Example 16

Preparation of 2-biphenyl-2-ylmethyl-5-hydroxy-1-methyl-6-oxo-1,6-dihydro-pyrimidine-4-carboxylic acid methylamide

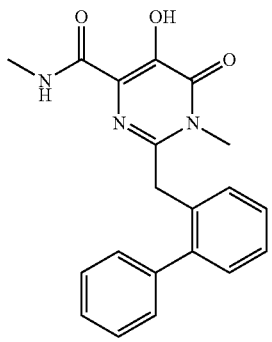 [SMILES: CNC(=O)c1nc(Cc2ccccc2-c2ccccc2)n(C)c(=O)c1O]

A sealed tube containing 2M solution of methylamine (1.71 ml, 3.42 mmol) in THF and methyl 2-(biphenyl-2-ylmethyl)-5-hydroxy-1-methyl-6-oxo-1,6-dihydropyrimidine-4-carboxylate (0.1 g, 285 μmol) was heated at 100° C. in a microwave oven for 20 min, cooled and filtered. The solid was stirred in MeOH, in the presence of Amberlyst 15 IE resin, at 60° C. for 5 min and then at room temperature for 1 h, filtered, evaporated to dryness and triturated with Et₂O to give the title compound as a white solid (0.040 g; 40%). LCMS: m/z=351 (MH+).

Example 17

Preparation of 2-biphenyl-2-ylmethyl-5-hydroxy-1-methyl-6-oxo-1,6-dihydro-pyrimidine-4-carboxylic acid isopropylamide

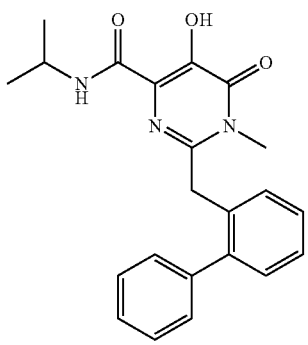 [SMILES: CC(C)NC(=O)c1nc(Cc2ccccc2-c2ccccc2)n(C)c(=O)c1O]

A sealed tube containing propan-2-amine (202 mg, 292 μl, 3.42 mmol), methyl 2-(biphenyl-2-ylmethyl)-5-hydroxy-1-methyl-6-oxo-1,6-dihydropyrimidine-4-carboxylate (0.1 g, 285 μmol) and THF (1.7 ml) was heated at 110° C. in a microwave oven for 20 minutes. The crude reaction mixture was cooled and evaporated to dryness. Purification by preparative HPLC provided the desired product as a light pink solid (0.015 g; 14%). LCMS: m/z=379 (MH+).

Example 18

Preparation of 2-biphenyl-2-ylmethyl-5-hydroxy-6-oxo-1,6-dihydro-pyrimidine-4-carboxylic acid methyl ester

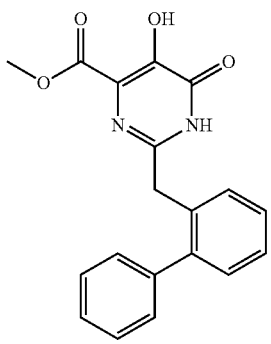 [SMILES: COC(=O)c1nc(Cc2ccccc2-c2ccccc2)[nH]c(=O)c1O]

A 1M solution of hydroxylamine hydrochloride in MeOH (15 ml) and 1M KOH solution in MeOH (15 ml) was combined at 0° C. After 10 minutes, the salt was removed by filtration and the filtrate was directly added to a flask containing 2-(biphenyl-2-yl)acetonitrile (0.50 g, 2.58 mmol) and was heated at 60° C. overnight. The cooled mixture was evaporated to dryness under reduced pressure and the residue was dissolve in EtOAc, washed with water, and brine, dried ($MgSO_4$) and evaporated to dryness. The residue was dissolved in chloroform (10 ml) and treated with dimethyl but-2-ynedioate (0.403 g, 2.84 mmol). The mixture was stirred at 60° C. for 1 h and then evaporated to dryness. The residue was diluted with xylenes (10 ml) and heated at 130° C. for 90 min. The cooled filtrate was filtered, triturated with EtOAc and dried under vacuum to give the title product as an off-white solid (0.161 g; 18%). LCMS: m/z=337 (MH+).

Example 19

Preparation of 2-biphenyl-2-ylmethyl-5-hydroxy-6-oxo-1,6-dihydro-pyrimidine-4-carboxylic acid

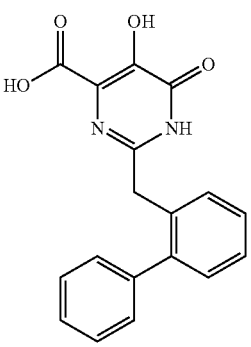 [SMILES: O=C(O)c1nc(Cc2ccccc2-c2ccccc2)[nH]c(=O)c1O]

The title product was prepared according to Example 15 using 2-biphenyl-2-ylmethyl-5-hydroxy-6-oxo-1,6-dihydro-pyrimidine-4-carboxylic acid methyl ester (0.050 g; 0.148 mmol). The title compound was produced as an off-white solid (0.020 g; 41%). LCMS: m/z=321 (M-H).

Example 20

Preparation of 2-biphenyl-2-ylmethyl-5-hydroxy-6-oxo-1,6-dihydro-pyrimidine-4-carboxylic acid methylamide

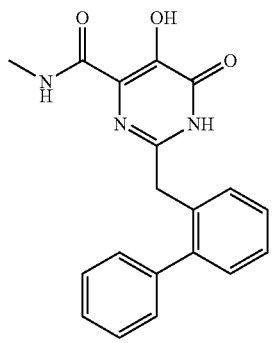

A sealed tube containing 2M solution of methylamine (2 ml, 4 mmol) in THF and methyl 2-(biphenyl-2-ylmethyl)-5-hydroxy-6-oxo-1,6-dihydropyrimidine-4-carboxylate (0.05 g, 163 µmol, Eq: 1.00) was heated at 150° C. in a microwave oven for 15 min, cooled and filtered. The solid was stirred in MeOH, in the presence of Amberlyst 15 IE resin, at 60° C. for 5 min and then at room temperature for 1 h, filtered, evaporated to dryness and triturated with Et$_2$O to give the title compound as a white solid (0.015 g; 27%). LCMS: m/z=336 (MH+).

Example 21

Preparation of 2-biphenyl-2-ylmethyl-5-hydroxy-6-oxo-1,6-dihydro-pyrimidine-4-carboxylic acid isopropylamide

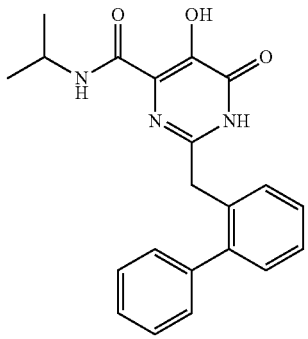 [SMILES: CC(C)NC(=O)c1nc(Cc2ccccc2-c2ccccc2)[nH]c(=O)c1O]

A sealed tube containing propan-2-amine (347 mg, 500 µl, 5.87 mmol), methyl 2-(biphenyl-2-ylmethyl)-5-hydroxy-6-oxo-1,6-dihydropyrimidine-4-carboxylate (0.50 g, 148 µmol) was heated at 150° C. in a microwave oven for 10 minutes. The crude reaction mixture was cooled and evaporated to dryness. The solid residue was stirred in MeOH, in the presence of Amberlyst 15 IE resin, at 60° C. for 5 min and then at room temperature for 1 h, filtered, evaporated to dryness and triturated with Et$_2$O to give the title compound as a white solid (0.012 g; 22%). LCMS: m/z=364 (MH+).

Example 22

Preparation of 2-biphenyl-2-ylmethyl-5-hydroxy-6-oxo-1,6-dihydro-pyrimidine-4-carboxylic acid benzylamide

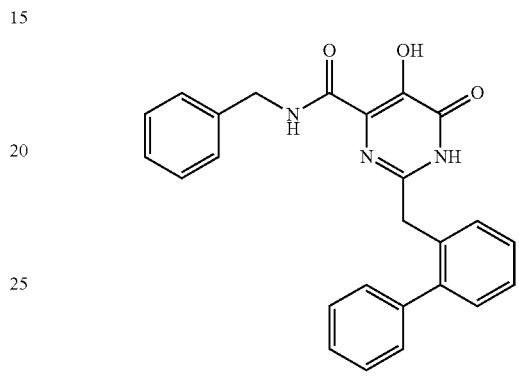

The synthesis was performed as in Example 21 using methyl 2-(biphenyl-2-ylmethyl)-5-hydroxy-6-oxo-1,6-dihydropyrimidine-4-carboxylate (0.070 g, 208 µmol) and benzylamine (0.5 ml; 4.58 mmol) to provide the title compound as an off-white solid (0.055 g; 64%). LCMS: m/z=412 (MH+).

Example 23

Preparation of 2-biphenyl-2-ylmethyl-5-hydroxy-6-oxo-1,6-dihydro-pyrimidine-4-carboxylic acid-4-fluorobenzylamide

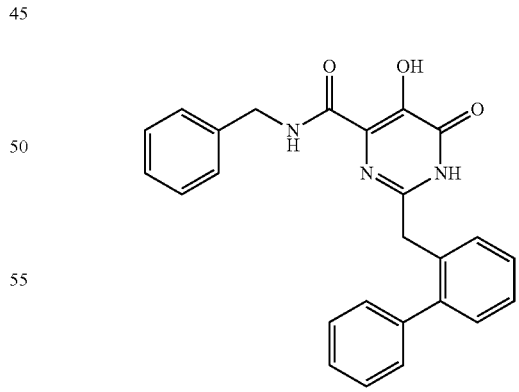

The synthesis performed as in Example 21 using methyl 2-(biphenyl-2-ylmethyl)-5-hydroxy-6-oxo-1,6-dihydropyrimidine-4-carboxylate (0.070 g, 208 µmol) and 4-fluorobenzylamine (0.5 ml; 4.38 mmol) to provide the title compound as an off-white solid (0.016 g; 18%). LCMS: m/z=430 (MH+).

Example 24

Preparation of 2-biphenyl-2-ylmethyl-5-hydroxy-6-oxo-1,6-dihydro-pyrimidine-4-carboxylic acid phenethylamide

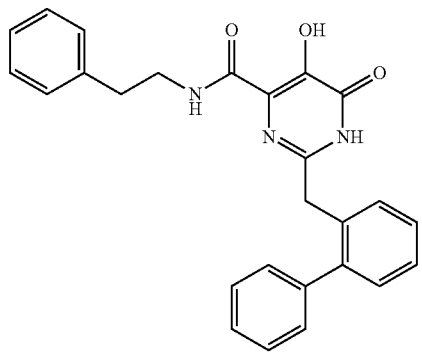 [SMILES: O=C(NCCc1ccccc1)c1nc(Cc2ccccc2-c2ccccc2)[nH]c(=O)c1O]

The synthesis was performed as in Example 21 using methyl 2-(biphenyl-2-ylmethyl)-5-hydroxy-6-oxo-1,6-dihydropyrimidine-4-carboxylate (0.10 g, 298 μmol) and phenethylamine (0.5 ml; 3.98 mmol) to provide the title compound as an off-white solid (0.054 g; 42%). LCMS: m/z=425 (MH+).

Example 25

Preparation of 2-biphenyl-2-ylmethyl-5-hydroxy-6-oxo-1,6-dihydro-pyrimidine-4-carboxylic acid isopropylamide

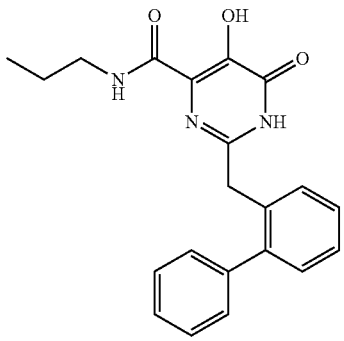 [SMILES: CCCNC(=O)c1nc(Cc2ccccc2-c2ccccc2)[nH]c(=O)c1O]

The synthesis was performed as in Example 21 using methyl 2-(biphenyl-2-ylmethyl)-5-hydroxy-6-oxo-1,6-dihydropyrimidine-4-carboxylate (0.10 g, 298 μmol) and isopropylamine (0.5 ml; 6.10 mmol) to provide the title compound as an off-white solid (0.059 g; 54%). LCMS: m/z=412 (MH+).

Example 26

Preparation of 2-biphenyl-2-ylmethyl-5-hydroxy-6-(pyrrolidine-1-carbonyl)-3H-pyrimidin-4-one

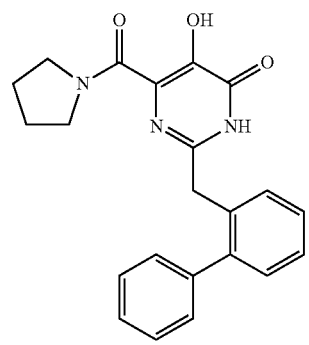 [SMILES: O=C(c1nc(Cc2ccccc2-c2ccccc2)[nH]c(=O)c1O)N1CCCC1]

The synthesis was performed as in Example 21 using methyl 2-(biphenyl-2-ylmethyl)-5-hydroxy-6-oxo-1,6-dihydropyrimidine-4-carboxylate (0.10 g, 298 μmol) and pyrrolidine (0.5 ml; 6.06 mmol) to provide the title compound as an off-white solid (0.059 g; 54%). LCMS: m/z=412 (MH+). LCMS: m/z=375 (MH+).

Example 27

Preparation of 2-(2,2-diphenyl-ethyl)-5-hydroxy-6-oxo-1,6-dihydro-pyrimidine-4-carboxylic acid methyl ester

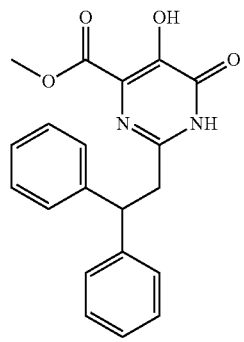 [SMILES: COC(=O)c1nc(CC(c2ccccc2)c2ccccc2)[nH]c(=O)c1O]

A solution of hydroxylamine hydrochloride (38.6 ml, 38.6 mmol) in MeOH was added to a solution of potassium hydroxide (38.6 ml, 38.6 mmol, Eq: 4) in MeOH at 0° C. The resulting mixture was filtered and the filtrate was added to a 150 mL round-bottomed flask containing 3,3-diphenylpropanenitrile (2 g, 9.65 mmol). The mixture was heated at reflux for 16 h, cooled and evaporated to dryness. The residue was dissolved in EtOAc, washed with brine, dried (MgSO$_4$) and evaporated to dryness. The crude product was dissolved in CHCl$_3$ (50 ml), treated with dimethyl but-2-ynedioate (1.65 g, 11.6 mmol, Eq: 1.2) and heated at reflux for 1 h and then evaporated to dryness. The residue was dissolved in xylene (10 ml), heated at 120° C. in a microwave oven for 4 h and evaporated to dryness. Chromatography (80 g SiO$_2$; 20 to 100% EtOAc in hexanes) gave the title product as an off-white solid (0.42; 12%). LCMS: m/z=348.9 (MH+).

Example 28

Preparation of 2-(2,2-diphenyl-ethyl)-5-hydroxy-6-oxo-1,6-dihydro-pyrimidine-4-carboxylic acid

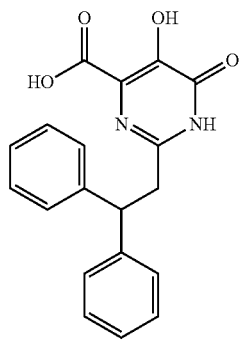 [SMILES: O=C(O)c1nc(CC(c2ccccc2)c2ccccc2)[nH]c(=O)c1O]

A solution of lithium hydroxide (21.9 mg, 913 μmol) in water (2 ml) was added to a flask containing a stirred solution of 2-(2,2-diphenyl-ethyl)-5-hydroxy-6-oxo-1,6-dihydro-pyrimidine-4-carboxylic acid methyl ester (0.160 g, 457 μmol) in THF (8 ml). The mixture was stirred at room temperature for 8 h, quenched with 1M HCl, extracted into EtOAc, washed with brine, dried (MgSO$_4$) and evaporated to dryness. Purification by preparative HPLC provided the desired product as a white solid (0.024 g; 15%). LCMS: m/z=337 (MH+).

Example 29

Preparation of 2-(2-bromo-4-fluoro-benzyl)-5-hydroxy-6-oxo-1,6-dihydro-pyrimidine-4-carboxylic acid methyl ester

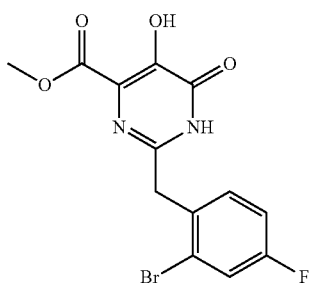 [SMILES: COC(=O)c1nc(Cc2ccc(F)cc2Br)[nH]c(=O)c1O]

A solution of potassium hydroxide (18.7 ml, 18.7 mmol) in methanol and hydroxylamine hydrochloride (18.7 ml, 18.7 mmol) in methanol were mixed, filtered and added to 2-(2-bromo-4-fluorophenyl)acetonitrile (1 g, 4.67 mmol) in MeOH and stirred at 60° C. for 24 h, evaporated to dryness. The residue was dissolved in chloroform (30.0 ml) and to this was added dimethyl but-2-ynedioate (730 mg, 5.14 mmol). The mixture was stirred at 60° C. for 24 h, cooled and evaporated to dryness. The residue was dissolved in xylene (10 ml) and heated at 120° C. for 2 h in microwave oven. The cooled residue was evaporated to dryness and then triturated with EtOAc, filtered and washed with Et$_2$O to give the title compound as a brown solid (0.21 g; 12%). LCMS: m/z=358 (MH+).

Example 30

Preparation of 2-(2-bromo-4-fluoro-benzyl)-5-hydroxy-6-oxo-1,6-dihydro-pyrimidine-4-carboxylic acid

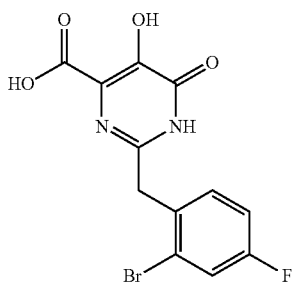 [SMILES: O=C(O)c1nc(Cc2ccc(F)cc2Br)[nH]c(=O)c1O]

A solution of lithium hydroxide monohydrate (23.5 mg, 560 μmol) in water (1 ml) was added to a stirred solution of methyl 2-(2-bromo-4-fluorobenzyl)-5,6-dihydroxypyrimidine-4-carboxylate (50 mg, 140 μmol) in THF (4 ml). The resulting mixture was stirred at room temperature for 24 h. The mixture was then acidified by the addition of Amberlyst resin, filtered and evaporated to dryness. The residue was triturated with Et$_2$O to give the title compound as a white solid (0.02 g; 41%). LCMS: m/z=344 (MH+).

Example 31

Preparation of 2-(2-bromo-4-fluoro-benzyl)-5-hydroxy-6-oxo-1,6-dihydro-pyrimidine-4-carboxylic acid amide

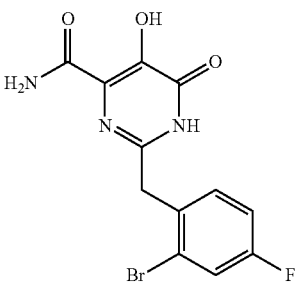 [SMILES: NC(=O)c1nc(Cc2ccc(F)cc2Br)[nH]c(=O)c1O]

A solution of ammonia in MeOH (1 mL, 7.00 mmol) was added to a flask containing methyl 2-(2-bromo-4-fluorobenzyl)-5,6-dihydroxypyrimidine-4-carboxylate (50 mg, 140 μmol). The mixture was heated at 120° C. for 15 minutes in a microwave oven. The resulting product was collected by filtration, suspended in MeOH with Amberlyst resin and heated. The warm mixture was filtered and evaporated to dryness. The residue was triturated with Et$_2$O and dried under vacuum to give the title compound as a white solid (0.032 g; 67%). LCMS: m/z=343 (MH+).

Example 32

Preparation of (2'-methyl-biphenyl-2-yl)-acetonitrile

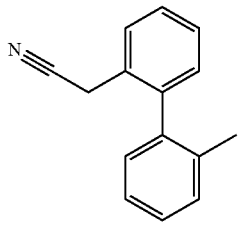 [SMILES: Cc1ccccc1-c1ccccc1CC#N]

In a vial, 2-bromophenylacetonitrile (2 g, 10.2 mmol), 2-methylphenylboronic acid (1.53 g, 11.2 mmol) and potassium carbonate (2.82 g, 20.4 mmol, Eq: 2) were combined with toluene (15.0 ml), ethanol (15 ml) and water (5 ml) to give a light brown suspension. The mixture was degassed with argon and then tetrakis(triphenylphosphine)palladium (0) (354 mg, 306 μmol) was added. The reaction mixture was heated at 90° C. for 12 h, cooled and poured into water and extracted with EtOAc. The organic phase was washed with brine, dried ($Na_2SO_4$) and evaporated to dryness under reduced pressure. Chromatography (silica gel, 0% to 5% EtOAc in hexanes) provided the title product as a colourless oil (1.57 g; 74%).

$^1$H NMR (300 MHz; $CDCl_3$) δ ppm 2.06 (s, 3 H), 3.43 (s, 2 H), 7.07-7.61 (m, 8 H).

Example 33

Preparation of 5-hydroxy-2-(2'-methyl-biphenyl-2-ylmethyl)-6-oxo-1,6-dihydro-pyrimidine-4-carboxylic acid methyl ester

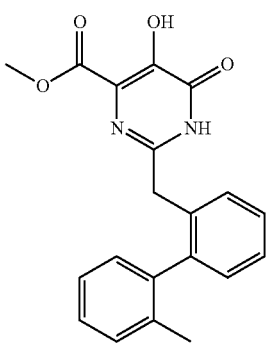 [SMILES: COC(=O)c1nc(Cc2ccccc2-c2ccccc2C)[nH]c(=O)c1O]

A solution of hydroxylamine hydrochloride (979 mg, 14.1 mmol) in methanol (15 ml) and a solution of potassium hydroxide (790 mg, 14.1 mmol) in methanol (15 ml) were combined at 0° C. Solid (KCl) was removed by filtration. The filtrate was added to 2-(2'-methylbiphenyl-2-yl)acetonitrile (1.46 g, 7.04 mmol) and heated at 60° C. overnight. An extra equivalent of $NH_2OH$ in MeOH solution was added and heating was continued for 5 h. The mixture was cooled and then concentrated in vacuo. The residue was taken up into $CHCl_3$ (30 ml) and to this was added dimethyl acetylenedicarboxylate (1.00 g, 7.04 mmol). The mixture was heated at 60° C. overnight, cooled and evaporated. The residue was transferred to a microwave vial and xylene (8 ml) was added. The vial was capped and heated in the microwave oven at 140° C. for 3 h, cooled. Chromatography (silica gel; 10% to 100% EtOAc in hexanes) provided the desired product as an off-white solid (0.003 g; 0.12%). LCMS: m/z=351 (MH+).

Example 34

Preparation (3'-methyl-biphenyl-2-yl)-acetonitrile

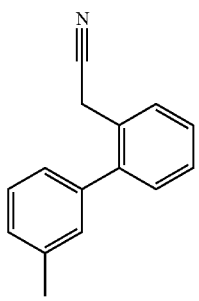 [SMILES: Cc1cccc(-c2ccccc2CC#N)c1]

In a vial, 2-bromophenylacetonitirle (2 g, 10.2 mmol), m-tolylboronic acid (1.66 g, 12.2 mmol) and potassium carbonate (2.82 g, 20.4 mmol) were combined with toluene (15 ml), ethanol (15 ml) and water (5 ml) to give a light brown suspension. The mixture was degassed with argon and then tetrakis(triphenylphosphine)palladium(0) (354 mg, 306 μmol) was added. The reaction mixture was heated to 90° C. and stirred overnight. The resulting cooled mixture was diluted with water and extracted into EtOAc. The organic phase was separated and washed with brine, dried ($Na_2SO_4$) and concentrated under reduced pressure. Chromatography (silica gel; 0% to 5% EtOAc in hexanes) provided the title product as a colourless oil (1.82 g; 80%).

$^1$H NMR (300 MHz; $CDCl_3$) δ ppm 2.42 (s, 3 H), 3.65 (s, 2 H), 7.03-7.62 (m, 8 H).

Example 35

Preparation of 5-hydroxy-2-(3'-methyl-biphenyl-2-ylmethyl)-6-oxo-1,6-dihydro-pyrimidine-4-carboxylic acid methyl ester

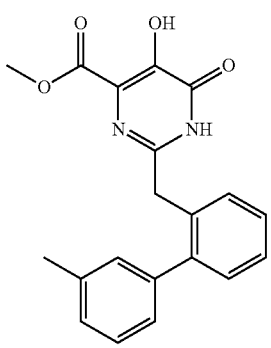 [SMILES: COC(=O)c1nc(Cc2ccccc2-c2cccc(C)c2)[nH]c(=O)c1O]

The compound was prepared using the same general procedure as Example 32 using 2-(3'-methylbiphenyl-2-yl)acetonitrile (1.81 g, 8.73 mmol). The title product was isolated as a white solid (0.07 g; 2%). LCMS: m/z=351 (MH+).

Example 36

Preparation of 5-hydroxy-2-(3'-methyl-biphenyl-2-ylmethyl)-6-oxo-1,6-dihydro-pyrimidine-4-carboxylic acid amide

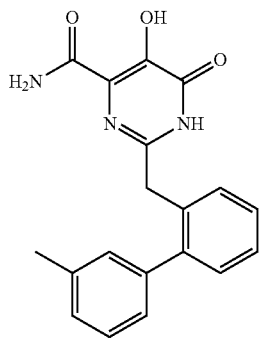 [SMILES: Cc1cccc(-c2ccccc2Cc2nc(C(N)=O)c(O)c(=O)[nH]2)c1]

A mixture containing methyl 5-hydroxy-2-((3'-methylbiphenyl-2-yl)methyl)-6-oxo-1,6-dihydropyrimidine-4-carboxylate (55 mg, 157 μmol) and ammonia (7M in MeOH) (4 ml, 28.0 mmol) in MeOH (2 ml) was heated at 100° C. overnight. The cooled reaction mixture was concentrated in vacuo and then triturated from methanol to give the title product as an off-white solid (0.025 g; 47%). LCMS: m/z=336 (MH+).

Example 37

Preparation of 5-hydroxy-2-(3'-methyl-biphenyl-2-ylmethyl)-6-oxo-1,6-dihydro-pyrimidine-4-carboxylic acid

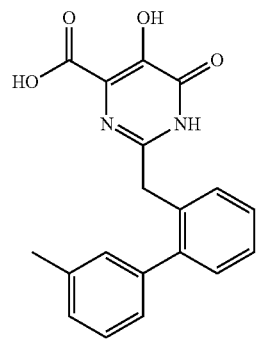

In a round-bottomed flask, methyl 5-hydroxy-2-((3'-methylbiphenyl-2-yl)methyl)-6-oxo-1,6-dihydropyrimidine-4-carboxylate (30 mg, 85.6 μmol) and lithium hydroxide hydrate (6.5 mg, 155 μmol) were combined with THF (2 ml) and water (1 ml) to give a colorless solution. The mixture was stirred at 50° C. for one day. Amberlyst (15, ion exchange resin) was added, the mixture was stirred for 10 min, filtered and evaporated to dryness. Trituration with EtOAc and hexanes provided the title compound as a white solid (0.011 g; 34%). LCMS: m/z=337 (MH+) 90% pure.

Example 38

Preparation of (2',5'-dimethyl-biphenyl-2-yl)-acetonitrile

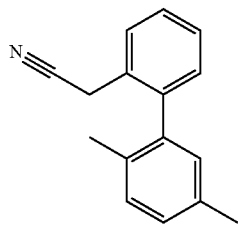 [SMILES: Cc1ccc(C)c(-c2ccccc2CC#N)c1]

The compound was prepared using the same general procedure as Example 33 using 2,5-dimethylphenylboronic acid (4.21 g, 28.1 mmol, Eq: 1.1). The title compound was prepared as a colourless oil (4.7 g; 83%).

$^1$H NMR (300 MHz; CDCl$_3$) δ ppm 2.01 (s, 3 H), 2.35 (s, 3 H), 3.44 (s, 2 H), 6.96 (s, 1 H), 7.08-7.24 (m, 3 H), 7.34-7.47 (m, 2 H), 7.53-7.62 (mm 1 H).

Example 39

Preparation of 2-(2',5'-dimethyl-biphenyl-2-ylmethyl)-5-hydroxy-6-oxo-1,6-dihydro-pyrimidine-4-carboxylic acid ethyl ester

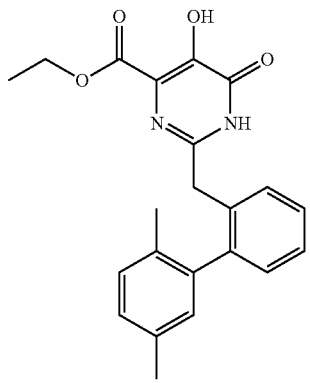 [SMILES: CCOC(=O)c1nc(Cc2ccccc2-c2cc(C)ccc2C)[nH]c(=O)c1O]

The compound was prepared using the same general procedure as Example 32 using 2-(2',5'-dimethylbiphenyl-2-yl) acetonitrile (4.7 g, 21.2 mmol) and diethyl but-2-ynedioate (3.61 g, 21.2 mmol). The title product was isolated as a white solid (0.84 g; 10%). LCMS: m/z=379 (MH+).

Example 40

Preparation of 2-(2',5'-dimethyl-biphenyl-2-ylmethyl)-5-hydroxy-6-oxo-1,6-dihydro-pyrimidine-4-carboxylic acid

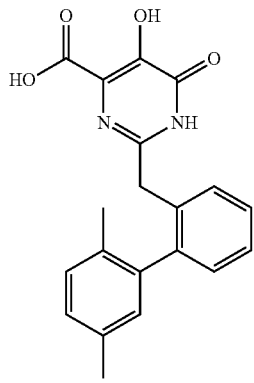 [SMILES: Cc1ccc(C)c(-c2ccccc2Cc2nc(C(=O)O)c(O)c(=O)[nH]2)c1]

The compound was prepared according to the same procedure as in Example 29 using 2-(2',5'-dimethyl-biphenyl-2-ylmethyl)-5-hydroxy-6-oxo-1,6-dihydro-pyrimidine-4-carboxylic acid ethyl ester (22 mg, 58.1 µmol) to provide the title compound as an off-white solid (0.018 g; 95% pure, 84% yield). LCMS: m/z=349 (M-H).

Example 41

Preparation of 2-cyclohexylmethyl-5-hydroxy-6-oxo-1,6-dihydro-pyrimidine-4-carboxylic acid methyl ester

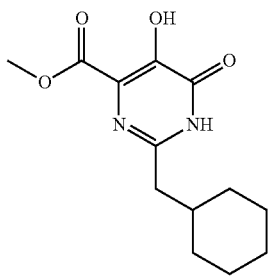 [SMILES: COC(=O)c1nc(CC2CCCCC2)[nH]c(=O)c1O]

The compound was prepared according to the same procedure as in Example 32 using 2-cyclohexylacetonitrile (2.5 g, 20.3 mmol). The title product was isolated as a white solid (0.060 g; 1%). LCMS: m/z=280 (MH+).

Example 42

Preparation of 2-cyclohexylmethyl-5-hydroxy-6-oxo-1,6-dihydro-pyrimidine-4-carboxylic acid methylamide

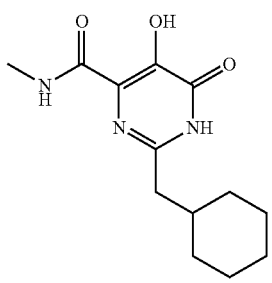 [SMILES: CNC(=O)c1nc(CC2CCCCC2)[nH]c(=O)c1O]

A mixture of methyl 2-(cyclohexylmethyl)-5-hydroxy-6-oxo-1,6-dihydropyrimidine-4-carboxylate (30 mg, 113 µmol), methylamine (2M in THF) (1.5 ml, 3.00 mmol) and MeOH (10 ml) was heated in a microwave oven at 140° C. for 40 min. The cooled reaction mixture was concentrated in vacuo. The residue was heated in a mixture of MeOH and Amberlyst until all the product had dissolved. The resin was removed by filtration and the filtrate was evaporated to dryness under reduced pressure to give the title compound as an off-white solid (0.011 g; 35% with 95% purity). LCMS: m/z=266 (MH+).

Example 43

Preparation of 2-(2-bromo-benzyl)-5-hydroxy-6-oxo-1,6-dihydro-pyrimidine-4-carboxylic acid methyl ester

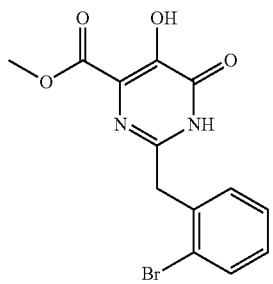 [SMILES: COC(=O)c1nc(Cc2ccccc2Br)[nH]c(=O)c1O]

The compound was prepared according to the same procedure as in Example 18 using 2-(2-bromophenyl)acetonitrile (0.50 g, 2.5 mmol) and dimethylacetylenedicarboxylate (0.40 g, 2.81 mmol). This provided the title product as a white solid (0.084 g; 9%). LCMS: m/z=340 (MH+).

Example 44

Preparation of 5-acetoxy-2-(2-bromo-benzyl)-6-oxo-1,6-dihydro-pyrimidine-4-carboxylic acid methyl ester

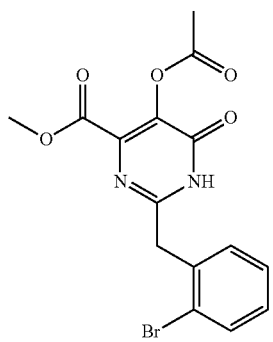 [SMILES: COC(=O)c1nc(Cc2ccccc2Br)[nH]c(=O)c1OC(C)=O]

In a round-bottomed flask, methyl 2-(2-bromobenzyl)-5,6-dihydroxypyrimidine-4-carboxylate (300 mg, 885 µmol) was combined with DCM (10 ml) to give a brown suspension. Acetyl chloride (1M in DCM) (2.21 ml, 2.21 mmol) was added slowly at room temperature. The mixture was stirred for one hour and then poured onto aqueous saturated NH$_4$Cl solution and extracted with DCM. The organic phase was washed with brine solution, dried (Na$_2$SO$_4$), and evaporated to dryness under reduced pressure. Chromatography (SiO$_2$; DCM) provided the title product as a white solid (0.33 g; 97%). LCMS: m/z=381/383 (MH+).

Example 45

Preparation of 2-(2-bromo-benzyl)-5-hydroxy-6-oxo-1,6-dihydro-pyrimidine-4-carboxylic acid methylamide

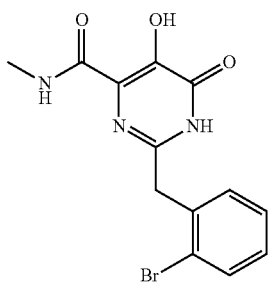 [SMILES: CNC(=O)c1nc(Cc2ccccc2Br)[nH]c(=O)c1O]

The compound was prepared according to the same procedure as in Example 20 using 2-(2-bromo-benzyl)-5-hydroxy-6-oxo-1,6-dihydro-pyrimidine-4-carboxylic acid methyl ester (0.08 g; 0.236 mmol). This gave the title compound as a white solid (0.032 g; 40%). LCMS: m/z=339 (MH+).

Example 46

Preparation of 2-(2-bromo-benzyl)-5-hydroxy-6-oxo-1,6-dihydro-pyrimidine-4-carboxylic acid iso-propylamide

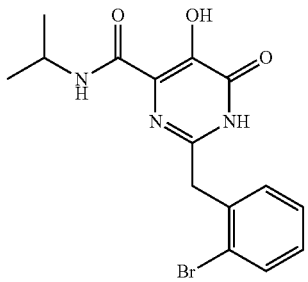 [SMILES: CC(C)NC(=O)c1nc(Cc2ccccc2Br)[nH]c(=O)c1O]

The compound was prepared according to the same procedure as in Example 21 using 2-(2-bromo-benzyl)-5-hydroxy-6-oxo-1,6-dihydro-pyrimidine-4-carboxylic acid methyl ester (0.08 g; 0.236 mmol) and isopropylamine (0.4 ml; 4.7 mmol). This gave the title compound as a white solid (0.021 g; 24%). LCMS: m/z=367 (MH+).

Example 47

Preparation of 2-(2-bromo-benzyl)-5-hydroxy-6-oxo-1,6-dihydro-pyrimidine-4-carboxylic acid 4-chloro-benzylamide

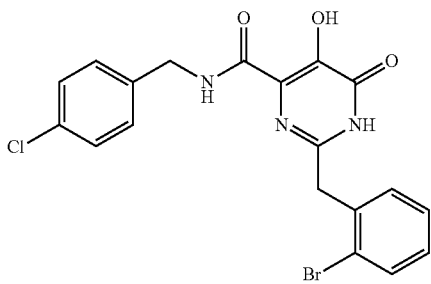 [SMILES: O=C(NCc1ccc(Cl)cc1)c1nc(Cc2ccccc2Br)[nH]c(=O)c1O]

The compound was prepared according to the same procedure as in Example 21 using 2-(2-bromo-benzyl)-5-hydroxy-6-oxo-1,6-dihydro-pyrimidine-4-carboxylic acid methyl ester (0.08 g; 0.236 mmol) and 4-chlorobenzylamine (0.5 ml; 4.1 mmol). The title compound was prepared as a white solid (0.042 g; 39%). LCMS: m/z=449 (MH+).

Example 48

Preparation of 2-(2-bromo-benzyl)-5-hydroxy-6-oxo-1,6-dihydro-pyrimidine-4-carboxylic acid 4-fluoro-benzylamide

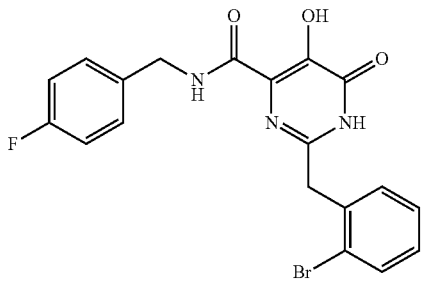 [SMILES: O=C(NCc1ccc(F)cc1)c1nc(Cc2ccccc2Br)[nH]c(=O)c1O]

The compound was prepared according to the same procedure as in Example 21 using 2-(2-bromo-benzyl)-5-hydroxy-6-oxo-1,6-dihydro-pyrimidine-4-carboxylic acid methyl ester (0.08 g; 0.236 mmol) and 4-fluorobenzylamine (0.5 ml; 4.4 mmol). This gave the title compound as a white solid (0.072 g; 70%). LCMS: m/z=433 (MH+).

Example 49

Preparation of 2-(3-benzyl-3H-imidazol-4-ylm-ethyl)-5-hydroxy-6-oxo-1,6-dihydro-pyrimidine-4-carboxylic acid ethyl ester

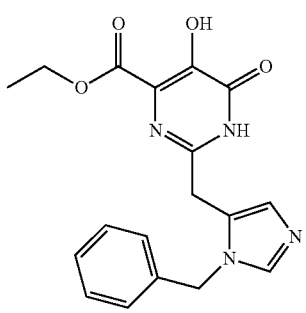 [SMILES: CCOC(=O)c1nc(Cc2cncn2Cc2ccccc2)[nH]c(=O)c1O]

A solution of hydroxylamine hydrochloride (2.85 g, 41.1 mmol) in methanol (25 ml) and a solution of potassium hydroxide (2.3 g, 41.1 mmol) in methanol (25 ml) were combined at 0° C. The resulting salt was removed by filtration and the filtrate was immediately added to 2-(1-benzyl-1H-imidazol-5-yl)acetonitrile (1.62 g, 8.21 mmol). The resulting solution was heated at 60° C. overnight and then evaporated to dryness. The residue was taken up into CHCl$_3$ (100 ml), and diethyl but-2-ynedioate (1.4 g, 8.21 mmol) was added. The resulting mixture was heated at 60° C. overnight. After cooling, the crude reaction mixture was concentrated in vacuo. The residue was treated with water and EtOAc. The organic phase was separated, washed with brine, dried (Na$_2$SO$_4$) and concentrated in vacuo. The residue was heated in xylene (2.5 ml), at 140° C. in a microwave reactor for 40 min. The cooled mixture was evaporated to dryness, dissolved in MeOH, passed through Celite® and then evaporated to dryness under reduced pressure. Purification by preparative HPLC provided the desired product as a yellow solid (0.014 g; 0.36%). LCMS: m/z=355 (MH+) 75% purity.

Example 50

Preparation of 2-(2-bromo-5-trifluoromethyl-benzyl)-5-hydroxy-6-oxo-1,6-dihydro-pyrimidine-4-carboxylic acid methyl ester

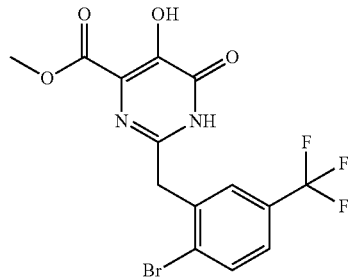 [SMILES: COC(=O)c1nc(Cc2cc(C(F)(F)F)ccc2Br)[nH]c(=O)c1O]

Preparation was performed following the general procedure used in Example 18 using 2-bromo-5-(trifluoromethyl)phenylacetonitrile (1 g; 3.78 mmol) and dimethyl but-2-ynedioate (1.09 g, 7.67 mmol) to provide the desired product as an off-white solid (0.29 g; 16%). LCMS: m/z=408 (MH+).

Example 51

Preparation of 2-(2-bromo-5-trifluoromethyl-benzyl)-5-hydroxy-6-oxo-1,6-dihydro-pyrimidine-4-carboxylic acid methylamide

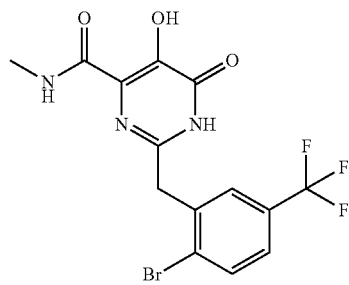 [SMILES: CNC(=O)c1nc(Cc2cc(C(F)(F)F)ccc2Br)[nH]c(=O)c1O]

The compound was prepared according to the same procedure as in Example 21 using 2-(2-bromo-5-trifluoromethyl-benzyl)-5-hydroxy-6-oxo-1,6-dihydro-pyrimidine-4-carboxylic acid methyl ester (0.080 g; 0.197 mmol) and 2M methylamine solution in THF (1 ml). This provided the title product as an off-white solid (0.043 g; 53%). LCMS: m/z=427 (MH+).

Example 52

Preparation of 5-hydroxy-1-methyl-2-methylsulfanyl-6-oxo-1,6-dihydro-pyrimidine-4-carboxylic acid methyl ester

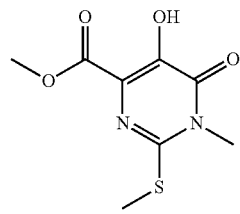

In a round-bottomed flask, thiocyanatomethane (17.5 g, 239 mmol) and N-methylhydroxylamine hydrochloride (20 g, 239 mmol) were combined with EtOH (100 ml) to give a light yellow solution. A solution of sodium carbonate (12.7 g, 120 mmol) in water (50 ml) was added slowly over 8 min at RT. The resulting mixture was stirred at RT for 2.5 days and then cooled in an ice bath. Dimethyl but-2-ynedioate (34.0 g, 239 mmol) was added slowly over 10 min and the resulting mixture was stirred for 2 hours, keeping the internal temperature below 22° C. Ice water and EtOAc were added. The organic layer was separated, washed with brine, dried over Na$_2$SO$_4$ and concentrated in vacuo. The resulting methyl 5-(2-methoxy-2-oxoethyl)-2-methyl-3-(methylthio)-2,5-dihydro-1,2,4-oxadiazole-5-carboxylate (62.7 g, 239 mmol) was placed in a round-bottomed flask, dissolved in xylene (110 ml), then heated at 140° C. for 48 hours, cooled and then evaporated to dryness to give the crude title product as a brown solid. LCMS: m/z=231 (MH+).

Example 53

Preparation 5-benzyloxy-1-methyl-2-methylsulfanyl-6-oxo-1,6-dihydro-pyrimidine-4-carboxylic acid methyl ester

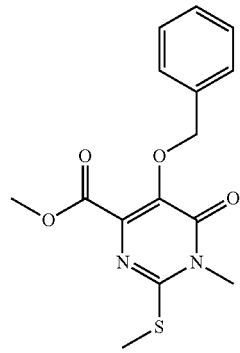 [SMILES: COC(=O)c1nc(SC)n(C)c(=O)c1OCc1ccccc1]

In a round-bottomed flask, methyl 5-hydroxy-1-methyl-2-(methylthio)-6-oxo-1,6-dihydropyrimidine-4-carboxylate (55.0 g, 239 mmol) and potassium carbonate (33.0 g, 239 mmol) were combined with DMF (200 ml) to give a black suspension. Benzyl bromide (40.9 g, 239 mmol) was added and the resulting mixture was stirred at room temperature for 3.5 days. The reaction was quenched by the addition of cold water. The mixture was filtered to provide a brown solid.

Chromatography (SiO$_2$; 10% to 50% EtOAc in hexanes) provided the desired product as an off-white solid (14.3 g; 18%). LCMS: m/z=321 (MH+).

Example 54

Preparation 5-benzyloxy-2-methanesulfonyl-1-methyl-6-oxo-1,6-dihydro-pyrimidine-4-carboxylic acid methyl ester

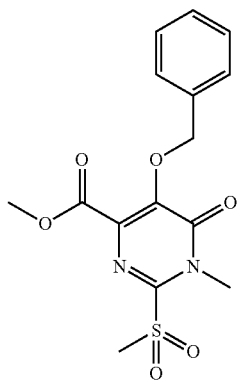 [SMILES: COC(=O)c1nc(S(C)(=O)=O)n(C)c(=O)c1OCc1ccccc1]

In a 1 L round-bottomed flask, methyl 5-(benzyloxy)-1-methyl-2-(methylthio)-6-oxo-1,6-dihydropyrimidine-4-carboxylate (5.57 g, 17.4 mmol) was combined with MeOH (400 ml) and DCM (50 ml). A solution of oxone (21.4 g, 34.8 mmol) in water (100 ml) was added. The mixture was stirred at room temperature for 5 hours and then evaporated to dryness. The residue was taken up into EtOAc, washed with 3N NaOH aqueous solution, water, and brine, dried over Na$_2$SO$_4$ and concentrated under reduced pressure to give the title compound as a white solid (3.7 g; 60%). LCMS: m/z=353 (MH+).

Example 55

Preparation of 2-amino-5-benzyloxy-1-methyl-6-oxo-1,6-dihydro-pyrimidine-4-carboxylic acid methyl ester

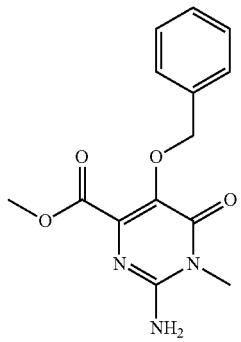

In a round-bottomed flask, methyl 5-(benzyloxy)-1-methyl-2-(methylsulfonyl)-6-oxo-1,6-dihydropyrimidine-4-carboxylate (3.65 g, 10.4 mmol) was combined with CH$_3$CN (50 ml) to give a colorless solution. Gaseous ammonia was bubbled at 25° C. for 20 min. The crude material was purified by flash chromatography (silica gel, 30% to 50% EtOAc in hexanes) and then through a second column (5% MeOH/DCM) to give the title product as a white solid. LCMS: m/z=290 (MH+).

Example 56

Preparation of 2-amino-5-benzyloxy-1-methyl-6-oxo-1,6-dihydro-pyrimidine-4-carboxylic acid methylamide

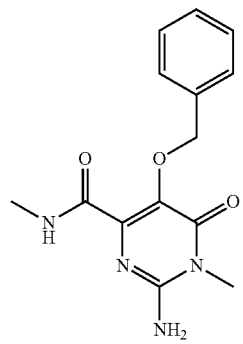 [SMILES: CNC(=O)c1nc(N)n(C)c(=O)c1OCc1ccccc1]

To a mixture of methyl 2-amino-5-(benzyloxy)-1-methyl-6-oxo-1,6-dihydropyrimidine-4-carboxylate (0.907 g, 3.14 mmol, Eq: 1.00), methylamine 2M in THF (12 ml, 24.0 mmol) was added. The mixture was heated in a microwave oven at 140° C. for 2 h. The crude reaction mixture was concentrated in vacuo to give the title product as an off-white solid (0.90 g; 100%). LCMS: m/z=289 (MH+).

Example 57

Preparation of 5-benzyloxy-1-methyl-6-oxo-2-m-tolylmethanesulfonylamino-1,6-dihydro-pyrimidine-4-carboxylic acid methylamide

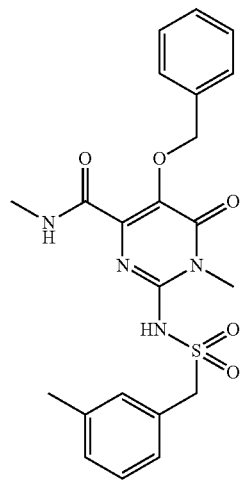 [SMILES: CNC(=O)c1nc(NS(=O)(=O)Cc2cccc(C)c2)n(C)c(=O)c1OCc1ccccc1]

Potassium tert-butoxide (75.9 mg, 676 μmol) was added to a solution of 2-amino-5-(benzyloxy)-N,1-dimethyl-6-oxo-1,6-dihydropyrimidine-4-carboxamide (150 mg, 520 μmol) in THF (15.0 ml) and DMF (3 ml). The resulting mixture was stirred for 10 min and then cooled with an ice-bath. To this mixture was slowly added a solution of (3-methylphenyl) methanesulfonyl chloride (140 mg, 684 μmol) in THF (1 ml). The reaction mixture was stirred at room temperature overnight. A further solution of (3-methylphenyl)methanesulfonyl chloride (140 mg, 684 µmol) in THF (1 ml) was added and then the mixture was stirred at room temperature for 48 hours. The resulting mixture was diluted with EtOAc, washed with saturated NaHCO₃ aqueous solution and brine. The organic layers were dried over Na₂SO₄ and concentrated in vacuo. Flash chromatography (silica gel, 0% to 2% MeOH in DCM) provided the desired product as a light yellow solid (0.070 g; 29%). LCMS: m/z=457 (MH+).

Example 58

Preparation of 5-hydroxy-1-methyl-6-oxo-2-m-tolyl-methanesulfonylamino-1,6-dihydro-pyrimidine-4-carboxylic acid methylamide

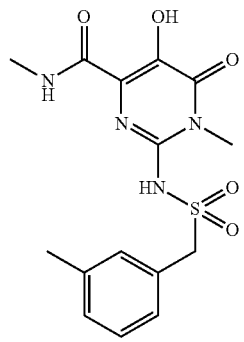 [SMILES: CNC(=O)c1nc(NS(=O)(=O)Cc2cccc(C)c2)n(C)c(=O)c1O]

Palladium on carbon 10% (20 mg, 18.8 µmol) was added to a round-bottomed flask containing a solution of 5-(benzyloxy)-N,1-dimethyl-6-oxo-2-(m-tolylmethylsulfonamido)-1,6-dihydro-pyrimidine-4-carboxamide (0.07 g, 153 µmol) in ethyl acetate (5 ml) and MeOH (5 ml). The resulting mixture was degassed by nitrogen, evacuated and purged with hydrogen. The mixture was stirred at room temperature under an atmosphere of hydrogen for one hour, filtered and evaporated to dryness under reduced pressure. The residue was washed with hexane and DCM, and crystallized from MeOH/Et₂O to give the title compound as an off-white solid (0.03 g; 53%). LCMS m/z=367 (MH+).

Example 59

Preparation of 5-benzyloxy-2-(4-chloro-phenyl-methanesulfonylamino)-1-methyl-6-oxo-1,6-dihydro-pyrimidine-4-carboxylic acid methylamide

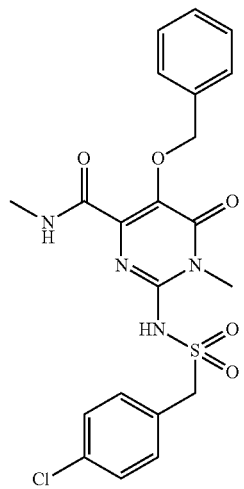 [SMILES: CNC(=O)c1nc(NS(=O)(=O)Cc2ccc(Cl)cc2)n(C)c(=O)c1OCc1ccccc1]

In a round-bottomed flask, 2-amino-5-(benzyloxy)-N,1-dimethyl-6-oxo-1,6-dihydropyrimidine-4-carboxamide (250 mg, 867 µmol, Eq: 1.00) was combined with THF (20 ml) to give a white suspension. DMF (4 ml) was added followed by potassium tert-butoxide (117 mg, 1.04 mmol, Eq: 1.2). The resulting mixture was stirred at room temperature for 10 min, then cooled with an ice bath. To this was slowly added a solution of (4-chlorophenyl)methanesulfonyl chloride (240 mg, 1.07 mmol, Eq: 1.23) in THF (1 ml). After stirring at room temperature for 14 h, further t-BuOK (234 mgs) was added. The mixture was stirred for 5 min, cooled in the ice bath and then further (4-chlorophenyl)methanesulfonyl chloride (240 mg, 1.07 mmol) was added. The reaction mixture was stirred for 72 hours at RT and then diluted with EtOAc, washed with saturated aqueous NaHCO₃ solution and brine. Some solid precipitated in the EtOAc solution and was collected by filtration. The remaining filtrate was evaporated to dryness, purified by flash chromatography (silica gel, 2% to 6% MeOH in DCM) and then triturated by EtOAc/Hex. The solids were combined to give the desired product as a white solid (0.210 g; 51%). LCMS m/z=477 (MH+).

Example 60

Preparation of 2-(4-chloro-phenylmethanesulfonylamino)-5-hydroxy-1-methyl-6-oxo-1,6-dihydro-pyrimidine-4-carboxylic acid methylamide and 5-hydroxy-1-methyl-6-oxo-2-phenylmethanesulfonylamino-1,6-dihydro-pyrimidine-4-carboxylic acid methylamide

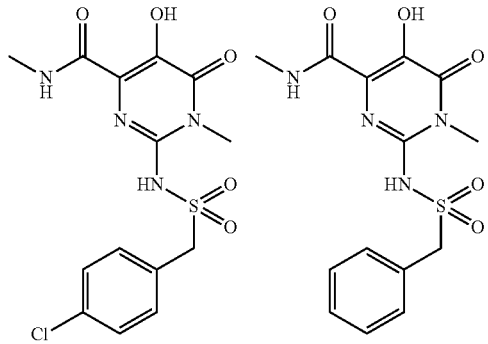

In a round-bottomed flask, 5-(benzyloxy)-2-((4-chlorophenyl)methylsulfonamido)-N,1-dimethyl-6-oxo-1,6-dihydropyrimidine-4-carboxamide (0.16 g, 335 µmol) was combined with ethyl acetate (40 ml) and MeOH (40.0 ml) to give a white suspension. Palladium on carbon 5% (50 mg, 470 µmol) was added and the solution was degassed by nitrogen. The mixture was stirred at room temperature under an atmosphere of hydrogen (balloon) for one hour and then the catalyst was removed by filtration and the filtrate was evaporated to dryness. Purification by preparative HPLC yielded:

2-(4-Chloro-phenylmethanesulfonylamino)-5-hydroxy-1-methyl-6-oxo-1,6-dihydro-pyrimidine-4-carboxylic acid methylamide as a white amorphous solid (0.026 g; 20%). LCMS: m/z=387 (MH+).

5-Hydroxy-1-methyl-6-oxo-2-phenylmethanesulfonylamino-1,6-dihydro-pyrimidine-4-carboxylic acid methylamide as a white amorphous solid (0.022 g; 17%). LCMS: m/z=353 (MH+).

Example 61

Preparation of 5-benzyloxy-1-methyl-6-oxo-2-p-tolylmethanesulfonyl-amino-1,6-dihydro-pyrimidine-4-carboxylic acid methylamide

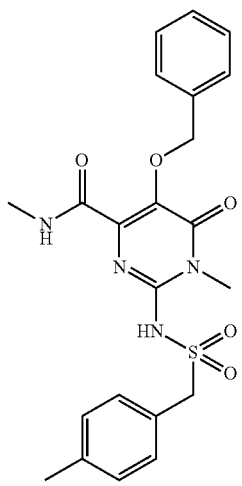

Potassium tert-butoxide (93.8 mg, 836 µmol) was added to a solution of 2-amino-5-(benzyloxy)-N,1-dimethyl-6-oxo-1,6-dihydropyrimidine-4-carboxamide (110 mg, 380 µmol) in THF (10 ml) in DMF (2 ml) [Comment: please check]. After 10 min., the reaction mixture was cooled by an ice bath and then a solution of (4-methylphenyl)methanesulfonyl chloride (93.7 mg, 458 µmol) in THF (2 ml) was added. After 70 min., EtOAc and 1 N NaOH aqueous solution were added. The organic phase was extracted with EtOAc and then with DCM. The combined organic phases were washed with water, and brine, dried over Na$_2$SO$_4$ and evaporated to dryness. Chromatography (silica gel, 0 to 2% MeOH in DCM) provided the title compound as a pale yellow solid (0.080 g; 46%). LCMS: m/z=457 (MH+).

Example 62

Preparation of 5-hydroxy-1-methyl-6-oxo-2-p-tolyl-methanesulfonylamino-1,6-dihydro-pyrimidine-4-carboxylic acid methylamide

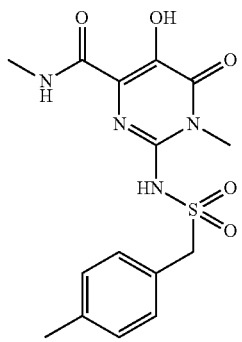 [SMILES: CNC(=O)c1nc(NS(=O)(=O)Cc2ccc(C)cc2)n(C)c(=O)c1O]

A mixture of 5-(benzyloxy)-N, 1-dimethyl-6-oxo-2-(p-tolylmethylsulfonamido)-1,6-dihydro-pyrimidine-4-carboxamide (80 mg, 175 µmol), palladium on carbon (186 mg, 87.6 µmol), MeOH (5 ml) and ethyl acetate (5 ml) was placed under an atmosphere of hydrogen. After stirring for 1.5 hour, the reaction mixture was filtered and evaporated to dryness. Crystallization from MeOH provided the title product as an off-white solid (0.045 g; 70%). LCMS: m/z=367 (MH+).

Example 63

Preparation of 5-benzyloxy-2-cyclohexylmethyl-1-methyl-6-oxo-1,6-dihydropyrimidine-4-carboxylic acid methyl ester

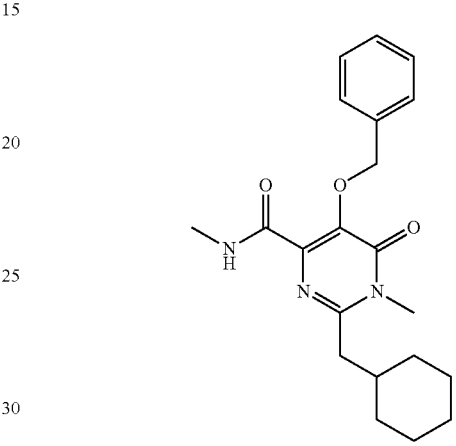

Cyclohexylmethylmagnesium bromide solution (1.77 ml; 885 µM of 0.5M solution in THF) was added dropwise to a solution of 5-benzyloxy-2-methanesulfonyl-1-methyl-6-oxo-1,6-dihydro-pyrimidine-4-carboxylic acid methyl ester (0.26 g; 738 µM) in THF (10 ml). After stirring at room temperature for 1 h, the reaction mixture was quenched by the addition of saturated ammonium chloride solution. The product was extracted into EtOAc, washed with brine, dried (Na$_2$SO$_4$) and evaporated to dryness under reduced pressure to give the title product as a colourless oil (0.040 g; 70%). LCMS: m/z=367 (MH+).

Example 64

Preparation of 2-cyclohexylmethyl-5-hydroxy-1-methyl-6-oxo-1,6-dihydro-pyrimidine-4-carboxylic acid methyl ester

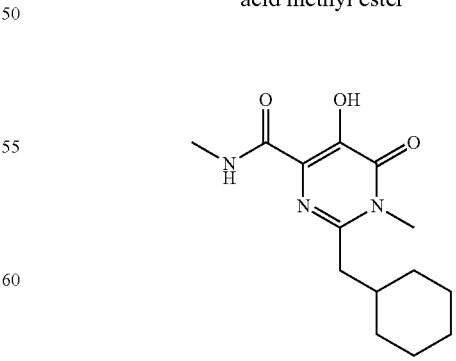

A mixture of methyl 5-(benzyloxy)-2-(cyclohexylmethyl)-1-methyl-6-oxo-1,6-dihydropyrimidine-4-carboxylate (60 mg, 162 µmol) and 20% palladium hydroxide on carbon (11.4 mg, 16.2 μmol) in EtOAc (10 ml) was placed under an atmosphere of hydrogen and stirred at room temperature overnight. The mixture was filtered and then evaporated to dryness. Chromatography (SiO$_2$; 0 to 20% EtOAc in hexanes) gave the title product as a white solid (0.032 g; 70%). LCMS: m/z=281 (MH+).

| Structure | FRET | CPE |
|---|---|---|
| (methyl ester pyrimidine diol with 1-phenylcyclopentylmethyl) | IC$_{50}$ = 0.41 μM | IC$_{50}$ = 12 μM |
| (primary amide pyrimidine diol with 1-phenylcyclopentylmethyl) | IC$_{50}$ = 0.24 μM | IC$_{50}$ = 42 μM |
| (N-benzyl amide pyrimidine diol with 1-phenylcyclopentylmethyl) | IC$_{50}$ = 1.1 μM | inactive |
| (carboxylic acid pyrimidine diol with biphenylmethyl) | IC$_{50}$ = 0.04 μM | inactive |
| (N-benzyl amide pyrimidine diol with biphenylmethyl) | IC$_{50}$ = 16 μM | inactive |
| (carboxylic acid pyrimidine diol with 1-phenylcyclopentylmethyl) | IC$_{50}$ = 0.08 μM | IC$_{50}$ = 49 μM |
| (N-methyl amide pyrimidine diol with 1-phenylcyclopentylmethyl) | IC$_{50}$ = 0.14 μM | IC$_{50}$ = 22 μM |
| (N-methyl amide pyrimidine diol with biphenylmethyl) | IC$_{50}$ = 0.66 μM | inactive |

-continued
| Structure | FRET | CPE |
|---|---|---|
| 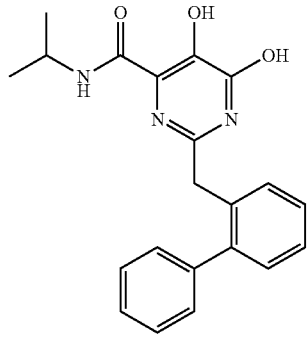 [SMILES: CC(C)NC(=O)c1nc(Cc2ccccc2-c2ccccc2)nc(O)c1O] | IC$_{50}$ = 8.2 μM | IC$_{50}$ = 23 μM |
| 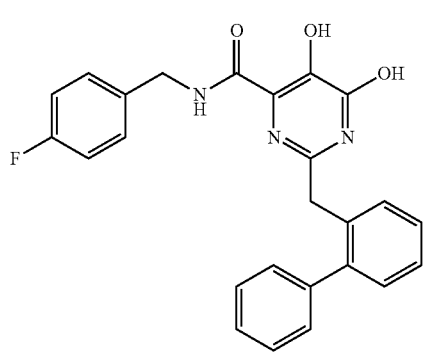 [SMILES: O=C(NCc1ccc(F)cc1)c1nc(Cc2ccccc2-c2ccccc2)nc(O)c1O] | IC$_{50}$ = 1.7 μM | IC$_{50}$ = 10 μM |
| 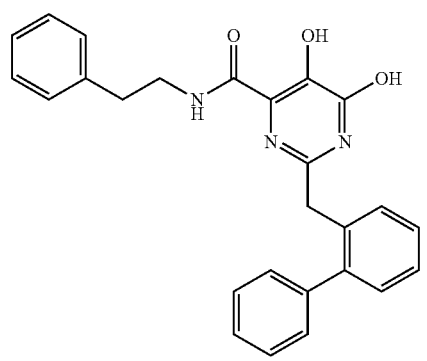 [SMILES: O=C(NCCc1ccccc1)c1nc(Cc2ccccc2-c2ccccc2)nc(O)c1O] | IC$_{50}$ = 3.8 μM | IC$_{50}$ = 8 μM |
| 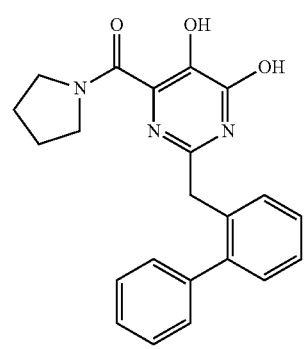 [SMILES: O=C(c1nc(Cc2ccccc2-c2ccccc2)nc(O)c1O)N1CCCC1] | IC$_{50}$ = 1.1 μM | IC$_{50}$ = 89 μM |
-continued
| Structure | FRET | CPE |
|---|---|---|
| 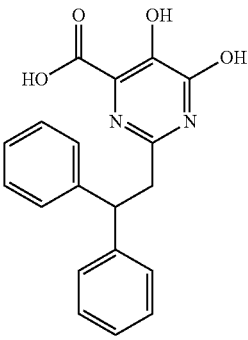 [SMILES: O=C(O)c1nc(CC(c2ccccc2)c2ccccc2)nc(O)c1O] | IC$_{50}$ = 2.5 μM | inactive |
| 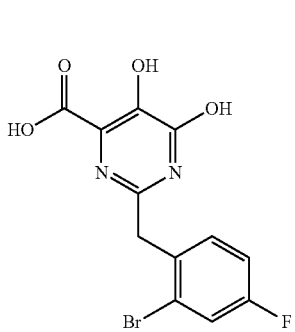 [SMILES: O=C(O)c1nc(Cc2ccc(F)cc2Br)nc(O)c1O] | IC$_{50}$ = 0.18 μM | inactive |
| 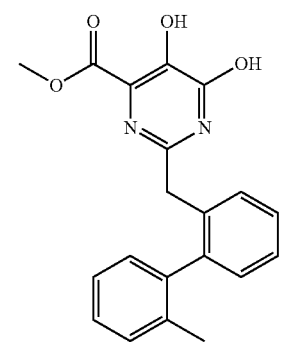 [SMILES: COC(=O)c1nc(Cc2ccccc2-c2ccccc2C)nc(O)c1O] | IC$_{50}$ = 0.12 μM | inactive |
| 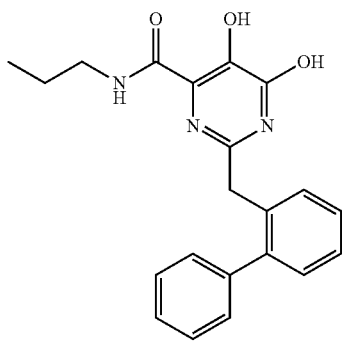 [SMILES: CCCNC(=O)c1nc(Cc2ccccc2-c2ccccc2)nc(O)c1O] | IC$_{50}$ = 8.8 μM | not determ. |

-continued

| Structure | FRET | CPE |
|---|---|---|
| (ethyl 5,6-dihydroxy-2-((1-benzyl-1H-imidazol-5-yl)methyl)pyrimidine-4-carboxylate) | IC$_{50}$ = 9.5 µM | inactive |
| (methyl 2-(2-bromo-4-fluorobenzyl)-5,6-dihydroxypyrimidine-4-carboxylate) | IC$_{50}$ = 1.5 µM | inactive |
| (2-(2-bromo-4-fluorobenzyl)-5,6-dihydroxypyrimidine-4-carboxamide) | IC$_{50}$ = 2.7 µM | inactive |
| (methyl 2-((3'-methylbiphenyl-2-yl)methyl)-5,6-dihydroxypyrimidine-4-carboxylate) | IC$_{50}$ = 0.35 µM | not determ. |
| (2-((3'-methylbiphenyl-2-yl)methyl)-5,6-dihydroxypyrimidine-4-carboxamide) | IC$_{50}$ = 0.55 µM | not determ. |

-continued

| Structure | FRET | CPE |
|---|---|---|
| (ethyl 2-((2',5'-dimethylbiphenyl-2-yl)methyl)-5,6-dihydroxypyrimidine-4-carboxylate) | IC$_{50}$ = 0.22 µM | IC$_{50}$ = 9.1 µM |
| (ethyl 2-(cyclohexylmethyl)-5,6-dihydroxypyrimidine-4-carboxylate) | IC$_{50}$ = 3.2 µM | inactive |
| (methyl 5-acetoxy-2-(2-bromobenzyl)-6-hydroxypyrimidine-4-carboxylate) | IC$_{50}$ = 7.9 µM | inactive |
| (2-(2-bromobenzyl)-5,6-dihydroxy-N-methylpyrimidine-4-carboxamide) | IC$_{50}$ = 5.7 µM | inactive |

-continued
| Structure | FRET | CPE |
|---|---|---|
| 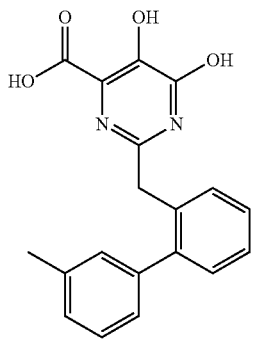 [SMILES: Cc1cccc(-c2ccccc2Cc2nc(O)c(O)c(C(=O)O)n2)c1] | IC$_{50}$ = 0.23 μM | inactive |
| 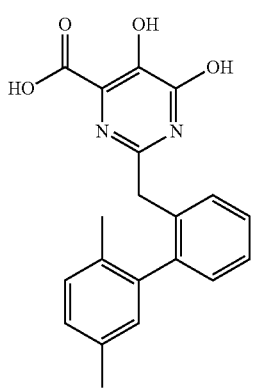 [SMILES: Cc1ccc(C)c(-c2ccccc2Cc2nc(O)c(O)c(C(=O)O)n2)c1] | IC$_{50}$ = 0.03 μM | inactive |
| 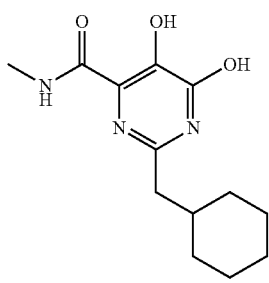 [SMILES: CNC(=O)c1nc(CC2CCCCC2)nc(O)c1O] | IC$_{50}$ = 6.5 μM | inactive |
| 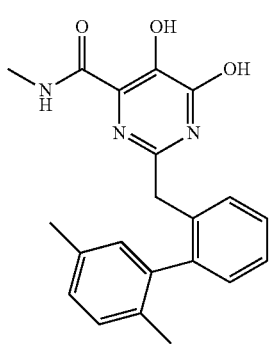 [SMILES: CNC(=O)c1nc(Cc2ccccc2-c2cc(C)ccc2C)nc(O)c1O] | IC$_{50}$ = 0.53 μM | inactive |
-continued
| Structure | FRET | CPE |
|---|---|---|
| 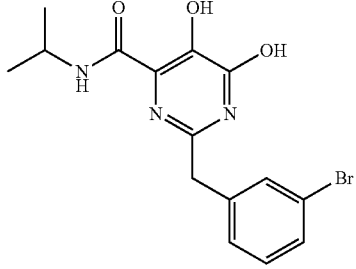 [SMILES: CC(C)NC(=O)c1nc(Cc2cccc(Br)c2)nc(O)c1O] | IC$_{50}$ = 23 μM | not determ. |
| 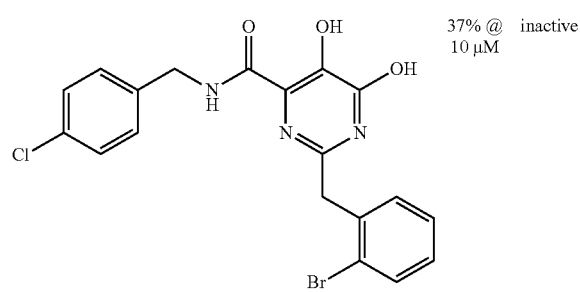 | 37% @ 10 μM | inactive |
| 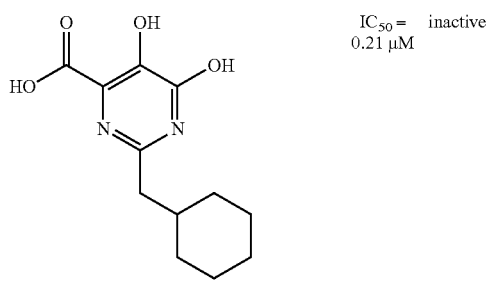 | IC$_{50}$ = 0.21 μM | inactive |
| 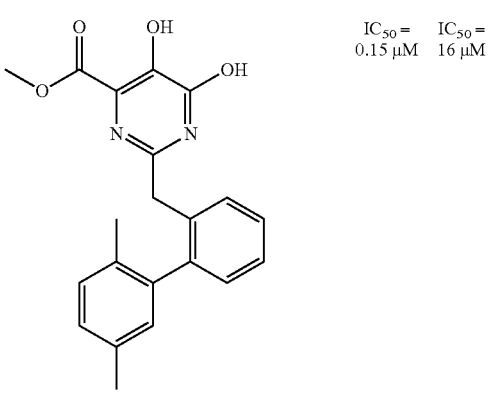 | IC$_{50}$ = 0.15 μM | IC$_{50}$ = 16 μM |
| 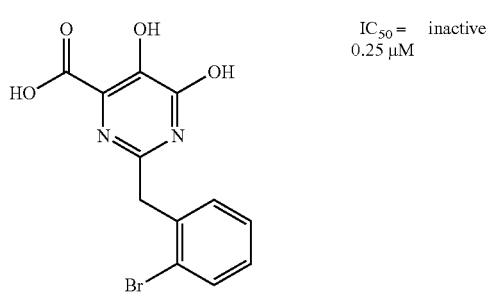 | IC$_{50}$ = 0.25 μM | inactive |

-continued

| Structure | FRET | CPE |
|---|---|---|
| 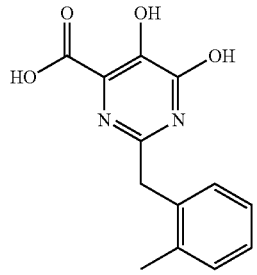 [SMILES: Cc1ccccc1Cc1nc(O)c(O)c(C(=O)O)n1] | IC$_{50}$ = 0.27 μM | inactive |
| 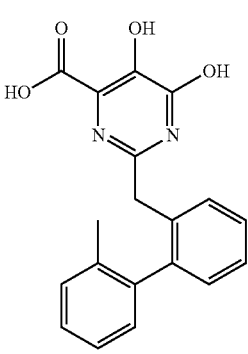 [SMILES: Cc1ccccc1-c1ccccc1Cc1nc(O)c(O)c(C(=O)O)n1] (F-benzyl amide, Br) | IC$_{50}$ = 27 μM | inactive |
| (methyl amide, 2,5-dimethylbiphenyl) | IC$_{50}$ = 0.53 μM | inactive |
| (tert-butyl ester, 2,5-dimethylbiphenyl) | IC$_{50}$ = 1.1 μM | IC$_{50}$ = 0.11 μM |

-continued

| Structure | FRET | CPE |
|---|---|---|
| 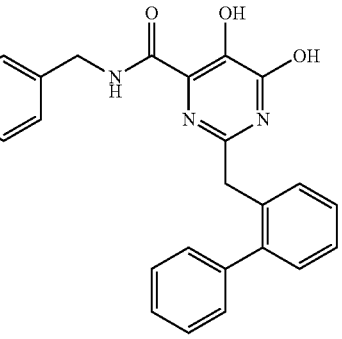 (4-Cl-benzyl amide, biphenyl) | IC$_{50}$ = 1.8 μM | inactive |
| (carboxylic acid, 2-methylbiphenyl) | IC$_{50}$ = 0.24 μM | inactive |
| 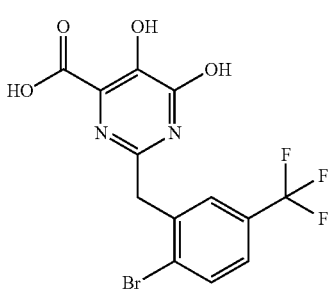 [SMILES: O=C(O)c1nc(Cc2cc(C(F)(F)F)ccc2Br)nc(O)c1O] (carboxylic acid, Br, CF$_3$) | IC$_{50}$ = 0.16 μM | inactive |
| 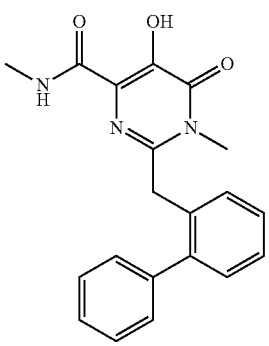 [SMILES: CNC(=O)c1nc(Cc2ccccc2-c2ccccc2)n(C)c(=O)c1O] (N-methyl pyrimidinone, methyl amide, biphenyl) | IC$_{50}$ = 23 μM | inactive |

-continued
| Structure | FRET | CPE |
|---|---|---|
| 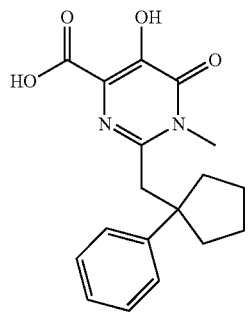 | IC$_{50}$ = 0.26 μM | inactive |
| 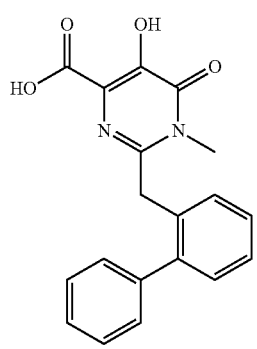 [SMILES: Cn1c(Cc2ccccc2-c2ccccc2)nc(C(=O)O)c(O)c1=O] | IC$_{50}$ = 1.3 μM | inactive |
| 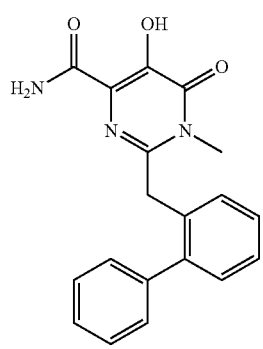 [SMILES: Cn1c(Cc2ccccc2-c2ccccc2)nc(C(N)=O)c(O)c1=O] | IC$_{50}$ = 1.3 μM | inactive |
| 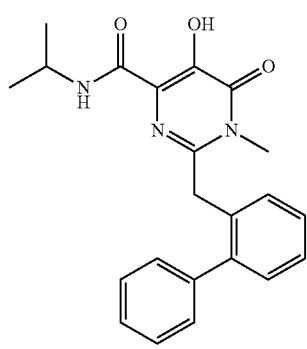 [SMILES: CC(C)NC(=O)c1nc(Cc2ccccc2-c2ccccc2)n(C)c(=O)c1O] | IC$_{50}$ = 14 μM | inactive |
-continued
| Structure | FRET | CPE |
|---|---|---|
| 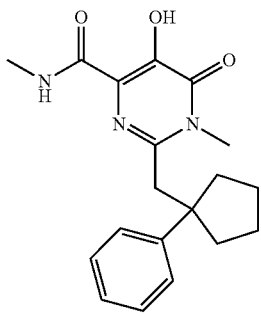 [SMILES: CNC(=O)c1nc(CC2(c3ccccc3)CCCC2)n(C)c(=O)c1O] | IC$_{50}$ = 0.41 μM | IC$_{50}$ = 11 μM |
| 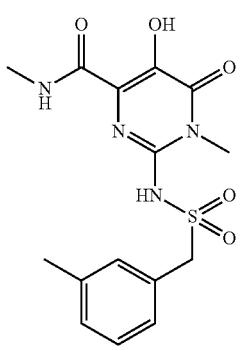 [SMILES: CNC(=O)c1nc(NS(=O)(=O)Cc2cccc(C)c2)n(C)c(=O)c1O] | IC$_{50}$ = 6.8 μM | inactive |
| 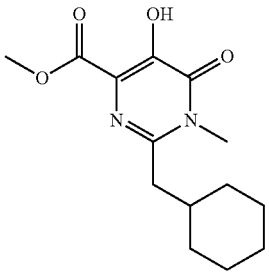 [SMILES: COC(=O)c1nc(CC2CCCCC2)n(C)c(=O)c1O] | 25% @ 10 μM | inactive |
| 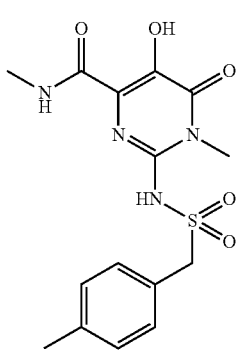 [SMILES: CNC(=O)c1nc(NS(=O)(=O)Cc2ccc(C)cc2)n(C)c(=O)c1O] | IC$_{50}$ = 13 μM | inactive | not determ. = not determined
The invention claimed is:
1. A compound having the general formula (Di), (Dii), or (Diii),
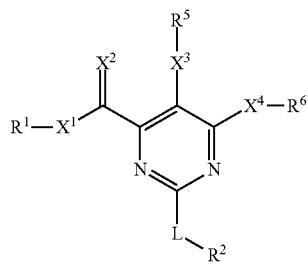
(Di)
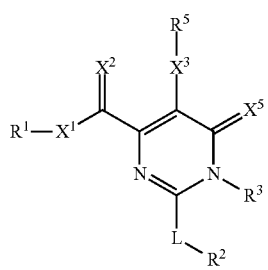
(Dii)
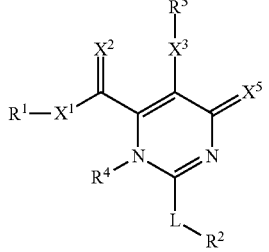
(Diii)

wherein
X¹ is O, S or NR*;
X² is O or S;
X³ is O or S;
X⁴ is O or S;
X⁵ is O or S;
L is —(CH$_2$)$_m$—, —NR*—SO$_2$— or —SO$_2$—NR*—;
m is 1 to 4;
R¹ is —H, -(optionally substituted C$_{1-6}$ alkyl), -(optionally substituted C$_{3-7}$ cycloalkyl), -(optionally substituted aryl), —C$_{1-4}$ alkyl-(optionally substituted aryl), —C(O)—O—R or —P(O)(OR)$_2$, if X¹ is NR* then R¹ and R* can optionally be bound together to form a 5- to 7-membered ring;
R² is a hydrocarbon group which contains from 5 to 20 carbon atoms and optionally 1 to 4 heteroatoms selected from O, N and S and which contains at least one ring, wherein the hydrocarbon group can be optionally substituted;
R³ is —H, -(optionally substituted C$_{1-6}$ alkyl), -(optionally substituted C$_{3-7}$ cycloalkyl), -(optionally substituted aryl), or —C$_{1-4}$ alkyl-(optionally substituted aryl);
R⁴ is —H, -(optionally substituted C$_{1-6}$ alkyl), -(optionally substituted C$_{3-7}$ cycloalkyl), -(optionally substituted aryl), or —C$_{1-4}$ alkyl-(optionally substituted aryl);
R⁵ is —H, —C(O)-(optionally substituted C$_{1-6}$ alkyl), or -(optionally substituted C$_{1-6}$ alkyl);
R⁶ is —H, —C(O)-(optionally substituted C$_{1-6}$ alkyl), or -(optionally substituted C$_{1-6}$ alkyl);
R* is —H, or —(C$_{1-6}$ alkyl); and
R** is —H, —(C$_{1-6}$ alkyl), —(C$_{3-7}$ cycloalkyl), -(aryl), or —C$_{1-4}$ alkyl-(aryl);
wherein the optional substituent of the alkyl group is selected from the group consisting of halogen, —CN, —NR*R*, —OH, and —O—C$_{1-6}$ alkyl; and
wherein the optional substituent of the cycloalkyl group, the aryl group or the hydrocarbon group is selected from the group consisting of —C$_{1-6}$ alkyl, -halogen, —CF$_3$, —CN, —X¹—R*, -aryl and —C$_{1-4}$ alkyl-aryl,
or a pharmaceutically acceptable salt, solvate, polymorph, codrug, cocrystal, prodrug, tautomer, racemate, enantiomer, or diastereomer or a mixture thereof,
with the proviso that the following compound

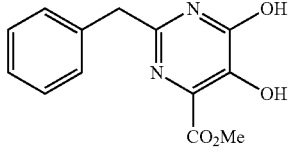 [SMILES: COC(=O)c1nc(Cc2ccccc2)nc(O)c1O]

is disclaimed.

2. A pharmaceutical composition comprising a compound having the general formula (Di), (Dii), or (Diii),

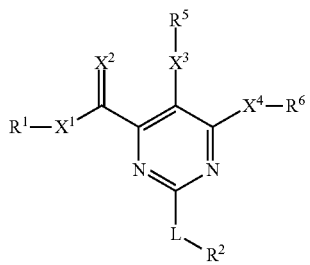

(Di)

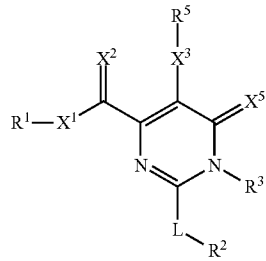

(Dii)

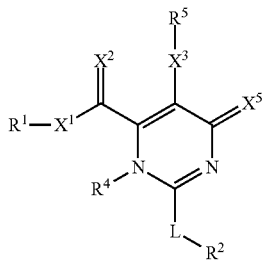

(Diii)

wherein
X¹ is O, S or NR*;
X² is O or S;
X³ is O or S;
X⁴ is O or S;
X⁵ is O or S;
L is —(CH$_2$)$_m$—, —NR*—SO$_2$— or —SO$_2$—NR*—;
m is 1 to 4;
R¹ is —H, -(optionally substituted C$_{1-6}$ alkyl), -(optionally substituted C$_{3-7}$ cycloalkyl), -(optionally substituted aryl), —C$_{1-4}$ alkyl-(optionally substituted aryl), —C(O)—O—R or —P(O)(OR)$_2$, if X¹ is NR* then R¹ and R* can optionally be bound together to form a 5- to 7-membered ring,
R² is a hydrocarbon group which contains from 5 to 20 carbon atoms and optionally 1 to 4 heteroatoms selected from O, N and S and which contains at least one ring, wherein the hydrocarbon group can be optionally substituted;
R³ is —H, -(optionally substituted C$_{1-6}$ alkyl), -(optionally substituted C$_{3-7}$ cycloalkyl), -(optionally substituted aryl), or —C$_{1-4}$ alkyl-(optionally substituted aryl);
R⁴ is —H, -(optionally substituted C$_{1-6}$ alkyl), -(optionally substituted C$_{3-7}$ cycloalkyl), -(optionally substituted aryl), or —C$_{1-4}$ alkyl-(optionally substituted aryl);
R⁵ is —H, —C(O)-(optionally substituted C$_{1-6}$ alkyl), or -(optionally substituted C$_{1-6}$ alkyl);
R⁶ is —H, —C(O)-(optionally substituted C$_{1-6}$ alkyl), or -(optionally substituted C$_{1-6}$ alkyl);
R* is —H, or —(C$_{1-6}$ alkyl); and
R** is —H, —(C$_{1-6}$ alkyl), —(C$_{3-7}$ cycloalkyl), -(aryl), or —C$_{1-4}$ alkyl-(aryl);
wherein the optional substituent of the alkyl group is selected from the group consisting of halogen, —CN, —NR*R*, —OH, and —O—C$_{1-6}$ alkyl; and
wherein the optional substituent of the cycloalkyl group, the aryl group or the hydrocarbon group is selected from the group consisting of —C$_{1-6}$ alkyl, -halogen, —CF$_3$, —CN, —X¹—R*, -aryl and —C$_{1-4}$ alkyl-aryl,
or a pharmaceutically acceptable salt, solvate, polymorph, codrug, cocrystal, prodrug, tautomer, racemate, enantiomer, or diastereomer or a mixture thereof,
and a pharmaceutically acceptable excipient.

3. A compound having the general formula (Di), (Dii), or (Diii),

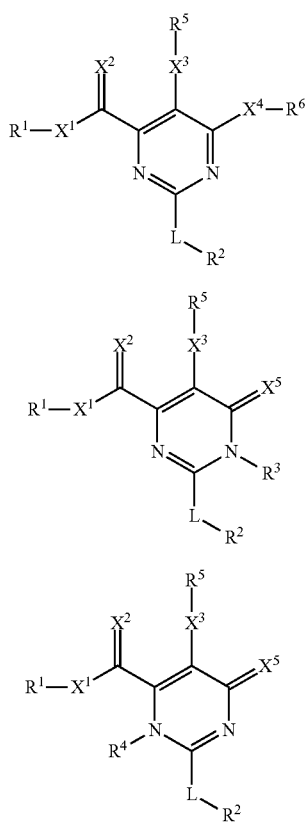

wherein
X¹ is O, S or NR*;
X² is O or S;
X³ is O or S;
X⁴ is O or S;
X⁵ is O or S;
L is —(CH$_2$)$_m$—, —NR*—SO$_2$— or —SO$_2$—NR*—;
m is 1 to 4;
R¹ is —H, -(optionally substituted C$_{1-6}$ alkyl), -(optionally substituted C$_{3-7}$ cycloalkyl), -(optionally substituted aryl), —C$_{1-4}$ alkyl-(optionally substituted aryl), —C(O)—O—R or —P(O)(OR)$_2$, if X¹ is NR* then R¹ and R* can optionally be bound together to form a 5- to 7-membered ring;
R² is a hydrocarbon group which contains from 5 to 20 carbon atoms and optionally 1 to 4 heteroatoms selected from O, N and S and which contains at least one ring, wherein the hydrocarbon group can be optionally substituted;
R³ is —H, -(optionally substituted C$_{1-6}$ alkyl), -(optionally substituted C$_{3-7}$ cycloalkyl), -(optionally substituted aryl), or —C$_{1-4}$ alkyl-(optionally substituted aryl);
R⁴ is —H, -(optionally substituted C$_{1-6}$ alkyl), -(optionally substituted C$_{3-7}$ cycloalkyl), -(optionally substituted aryl), or —C$_{1-4}$ alkyl-(optionally substituted aryl);
R⁵ is —H, —C(O)-(optionally substituted C$_{1-6}$ alkyl), or -(optionally substituted C$_{1-6}$ alkyl);
R⁶ is —H, —C(O)-(optionally substituted C$_{1-6}$ alkyl), or -(optionally substituted 0$_{1-6}$ alkyl);
R* is —H, or —(C$_{1-6}$ alkyl); and
R** is —H, —(C$_{1-6}$ alkyl), —(C$_{3-7}$ cycloalkyl), -(aryl), or —C$_{1-4}$ alkyl-(aryl);

wherein the optional substituent of the alkyl group is selected from the group consisting of halogen, —CN, —NR*R*, —OH, and —O—C$_{1-6}$ alkyl; and
wherein the optional substituent of the cycloalkyl group, the aryl group or the hydrocarbon group is selected from the group consisting of —C$_{1-6}$ alkyl, -halogen, —CF$_3$, —CN, —X¹—R*, -aryl and —C$_{1-4}$ alkyl-aryl,
or a pharmaceutically acceptable salt, solvate, polymorph, codrug, cocrystal, prodrug, tautomer, racemate, enantiomer, or diastereomer or a mixture thereof,
wherein the compound is for use in the treatment, amelioration or prevention of a viral disease.

4. The compound according to claim 3, wherein the viral disease is caused by Herpesviridae, Retroviridae, Filoviridae, Paramyxoviridae, Rhabdoviridae, Orthomyxoviridae, Bunyaviridae, Arenaviridae, Coronaviridae, Picornaviridae, Togaviridae, Flaviviridae.

5. The compound according to claim 4, wherein the viral disease is influenza.

6. A method of treating or ameliorating a viral disease, the method comprising administering to a patient in need thereof an effective amount of a compound having the general formula (Di), (Dii), or (Diii) according to claim 3, or a pharmaceutically acceptable salt, solvate, polymorph, codrug, cocrystal, prodrug tautomer, racemate, enantiomer, or diastereomer or mixture thereof.

7. The method according to claim 6, wherein the viral disease is caused by Herpesviridae, Retroviridae, Filoviridae, Paramyxoviridae, Rhabdoviridae, Orthomyxoviridae, Bunyaviridae, Arenaviridae, Coronaviridae, Picornaviridae, Togaviridae, or Flaviviridae.

8. The method according to claim 7, wherein the viral disease is influenza.

9. The compound according to claim 1, wherein m is 1 or 2.

10. The compound according to claim 1, wherein R¹ is —H or -(optionally substituted C$_{1-6}$ alkyl).

11. The compound according to claim 1, wherein R² is an optionally substituted aryl, optionally substituted heteroaryl or optionally substituted C$_{5-7}$ cycloalkyl.

12. The compound according to claim 1, wherein R² is

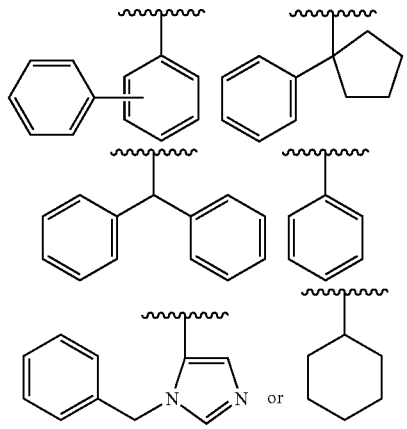

and wherein the heterocyclic group, phenyl group, cyclohexyl group or cyclopentyl group can be optionally substituted in any available position by a substituent which is independently selected from —C$_{1-6}$ alkyl, halogen, —CF$_3$, —CN, —OH, and —O—C$_{1-6}$ alkyl.

13. The compound according to claim 1, wherein L is —(CH$_2$)$_m$—, or —NR* —SO$_2$—.

14. The compound according to claim 1, wherein $X^1$ is O or NR*.

15. The method according to claim 6, wherein a further antiviral agent is to be administered concurrently or sequentially with the compound according to claim 3.

16. A pharmaceutical composition comprising:
(i) a compound having the general formula (Di), (Dii), or (Diii) as defined in claim 3; and
(ii) at least one polymerase inhibitor which is different from the compound having the general formula (Di), (Dii), or (Diii).

17. The pharmaceutical composition according to claim 16, wherein the at least one polymerase inhibitor which is different from the compound having the general formula (Di), (Dii), or (Diii) is selected from
(a) a compound having the general formula (A),

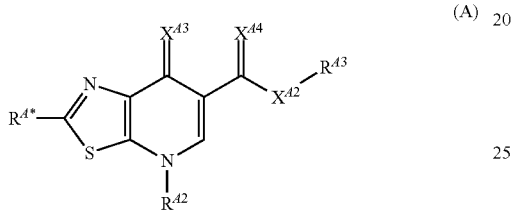

(A)

wherein
$R^{A*}$ is —H, -Hal, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), —$C_{1-4}$ alkyl-(optionally substituted aryl) or —$X^1$—$R^1$;
$X^{A1}$ is O, C(O), C(O)O, OC(O); S, SO, $SO_2$, $NR^{A4}$, $N(R^{A5})$C(O), or C(O)$NR^{A5}$;
$X^{A2}$ is O, S, or $NR^{A4}$;
$X^{A3}$ is O or S;
$X^{A4}$ is O or S;
$R^{A1}$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), or —$C_{1-4}$ alkyl-(optionally substituted aryl);
$R^{A2}$ is a hydrocarbon group which contains from 5 to 20 carbon atoms and optionally 1 to 4 heteroatoms selected from O, N and S and which contains at least one ring, wherein the hydrocarbon group can be optionally substituted;
$R^{A3}$ is —H, -(optionally substituted $C_{1-6}$ alkyl), -(optionally substituted $C_{3-7}$ cycloalkyl), -(optionally substituted aryl), or —$C_{1-4}$ alkyl-(optionally substituted aryl) if $X^{A2}$ is $NR^{A4}$ then $R^{A3}$ can also be —OH;
$R^{A4}$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), or —$C_{1-4}$ alkyl-(optionally substituted aryl) or if $X^{A1}$ is $NR^{A4}$, then $R^{A4}$ and $R^{A1}$ can be joined together to form a 5- to 7-membered ring, which can optionally contain O, S or further N or if $X^{A2}$ is $NR^{A4}$, then $R^{A4}$ and $R^{A3}$ can be joined together to form a 5- to 7-membered ring, which can optionally contain O, S or further N; and
$R^{A5}$ is —H, -(optionally substituted $C_{1-6}$ alkyl), -(optionally substituted $C_{3-7}$ cycloalkyl), -(optionally substituted aryl), -$C_{1-4}$ alkyl-(optionally substituted $C_{3-7}$ cycloalkyl), or —$C_{1-4}$ alkyl-(optionally substituted aryl); and
$R^{A6}$ is —H, or —$C_{1-6}$ alkyl;
wherein the optional substituent of the alkyl group is selected from the group consisting of halogen, —CN, —$NR^{A6}R^{A6}$, —OH, and —O—$C_{1-6}$ alkyl;
wherein the optional substituent of the cycloalkyl group, the aryl group or the hydrocarbon group is selected from the group consisting of —$C_{1-6}$ alkyl, halogen, —$CF_3$, —CN, —$X^{A1}$—$R^{A5}$ and —$C_{1-4}$ alkyl-aryl;
or a pharmaceutically acceptable salt, solvate, polymorph, codrug, cocrystal, prodruq, tautomer, racemate, enantiomer, or diastereomer or a mixture thereof, and
(b) a compound having the general formula (C),

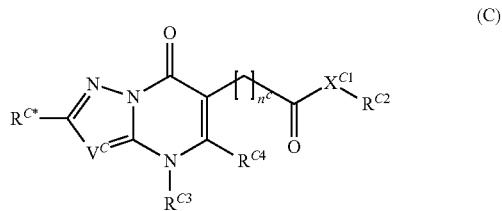

(C)

wherein
$V^C$ is N, or $CR^{C6}$;
$X^{C1}$ is O, S, or $NR^{C8}$;
$X^{C2}$ is $NR^{C5}$, $N(R^{C5})C(O)$, $C(O)NR^{C5}$, O, C(O), C(O)O, OC(O); S, SO, $SO_2$, $SO_2N(R^{C5})$ or $N(R^{C5})SO_2$;
$R^{C*}$ is —H, -Hal, -(optionally substituted $C_{1-6}$ alkyl), -(optionally substituted mono- or polycyclic group containing 3 to 20 carbon atoms and optionally 1 to 4 heteroatoms selected from O, N and S), —$C_{1-4}$ alkyl-(optionally substituted mono- or polycyclic group containing 3 to 20 carbon atoms and optionally 1 to 4 heteroatoms selected from O, N and S), or —$X^{C2}$—$R^{C1}$;
$R^{C1}$ is —H, -(optionally substituted $C_{1-6}$ alkyl), -(optionally substituted mono- or polycyclic group containing 3 to 20 carbon atoms and optionally 1 to 4 heteroatoms selected from O, N and S), —$C_{1-4}$ alkyl-(optionally substituted mono- or polycyclic group containing 3 to 20 carbon atoms and optionally 1 to 4 heteroatoms selected from O, N and S);
$R^{C2}$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), or —$C_{1-4}$ alkyl-(optionally substituted aryl) or if $X^{C1}$ is $NR^{C1}$, then $R^{C2}$ can also be —OH;
$R^{C3}$ is —H, —$R^{C7}$, or —$X^{C2}$—$R^{C7}$;
$R^{C4}$ is —H, -(optionally substituted $C_{1-6}$ alkyl), -(optionally substituted $C_{3-7}$ cycloalkyl), -(optionally substituted aryl), $C_{1-4}$ alkyl-(optionally substituted $C_{3-7}$ cycloalkyl), or —$C_{1-4}$ alkyl-(optionally substituted aryl);
$R^{C5}$ is —H, -(optionally substituted $C_{1-6}$ alkyl), -(optionally substituted $C_{3-7}$ cycloalkyl), -(optionally substituted aryl), —$C_{1-4}$ alkyl-(optionally substituted $C_{3-7}$ cycloalkyl), or —$C_{1-4}$ alkyl-(optionally substituted aryl);
$R^{C6}$ H, —$C_{1-6}$ alkyl, -aryl, halogen or CN;
$R^{C7}$ is -(optionally substituted hydrocarbon group which contains from 5 to 20 carbon atoms and optionally 1 to 4 heteroatoms selected from O, N and S and which contains at least one ring);

$R^{C8}$ is —H, or —$C_{1-6}$ alkyl; and $n^C$ is 0 to 4;

wherein the optional substituent of the alkyl group is selected from the group consisting of halogen, —CN, —$NR^{C5}R^{C5}$, —OH, and —O—$C_{1-6}$ alkyl;

wherein the optional substituent of the cycloalkyl group, the aryl group, the mono- or polycyclic group or the hydrocarbon group is selected from the group consisting of —$C_{1-6}$ alkyl, halogen, —$CF_3$, —CN, —$X^{c2}$—$R^{C8}$ and —$C_{1-4}$ alkyl-aryl;

or a pharmaceutically acceptable salt, solvate, polymorph, codrug, cocrystal, prodrug, tautomer, racemate, enantiomer, or diastereomer or a mixture thereof.

18. A pharmaceutical composition comprising:
(i) a compound having the general formula (Di), (Dii), or (Diii) according to claim 3; and
(ii) at least one neuramidase inhibitor.

19. A pharmaceutical composition comprising:
(i) a compound having the general formula (Di), (Dii), or (Diii) according to claim 3; and
(ii) at least one M2 channel inhibitor.

20. A pharmaceutical composition comprising:
(i) a compound having the general formula (Di), (Dii), or (Diii) according to claim 3; and
(ii) at least one alpha glucosidase inhibitor.

21. A pharmaceutical composition comprising:
(i) a compound having the general formula (Di), (Dii), or (Diii) according to claim 3; and
(ii) at least one ligand of another influenza target.

22. A pharmaceutical composition comprising:
(i) a compound having the general formula (Di), (Dii), or (Diii) according to claim 3; and
(ii) at least one medicament selected from antibiotics, anti-inflammatory agents, lipoxygenase inhibitors, EP ligands, bradykinin ligands, and cannabinoid ligands.

23. A method of treating or ameliorating a viral disease, the method comprising administering to a patient in need thereof an effective amount of a pharmaceutical composition according to any of claims 16 to 22.

24. The method according to claim 23, wherein the viral disease is caused by Herpesviridae, Retroviridae, Filoviridae, Paramyxoviridae, Rhabdoviridae, Orthomyxoviridae, Bunyaviridae, Arenaviridae, Coronaviridae, Picornaviridae, Togaviridae, or Flaviviridae.

25. The compound according to claim 1, wherein the compound having the general formula (Di), (Dii), or (Diii) exhibits a % reduction of at least about 30 % at 50 μM in a cytopathic effect (CPE) assay.

26. The compound according to claim 1, wherein the compound having the general formula (Di), (Dii), or (Diii) exhibits an $IC_{50}$ of at least about 40 μM in a fluorescence resonance energy transfer (FRET) endonuclease activity assay.

27. The method according to claim 23, wherein the viral disease is caused by influenza.

28. A pharmaceutical composition according to any one of claims 16-22, further comprising one or more pharmaceutically acceptable excipients and/or carriers.

* * * * *